(12) United States Patent
Hazen

(10) Patent No.: US 10,117,879 B2
(45) Date of Patent: Nov. 6, 2018

(54) TREATING AND PREVENTING DISEASE WITH TMA AND TMAO LOWERING AGENTS

(71) Applicant: The Cleveland Clinic Foundation, Cleveland, OH (US)

(72) Inventor: Stanley L. Hazen, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/610,145

(22) Filed: May 31, 2017

(65) Prior Publication Data

US 2017/0266208 A1   Sep. 21, 2017

Related U.S. Application Data

(63) Continuation of application No. 14/866,398, filed on Sep. 25, 2015, now Pat. No. 9,694,020.
(Continued)

(51) Int. Cl.
*A61K 31/00* (2006.01)
*A61K 31/616* (2006.01)
(Continued)

(52) U.S. Cl.
CPC .......... *A61K 31/616* (2013.01); *A61K 31/00* (2013.01); *A61K 31/13* (2013.01); *A61K 31/133* (2013.01);
(Continued)

(58) Field of Classification Search
CPC ...... A61K 31/00; A61K 31/13; A61K 31/133; A61K 31/205; A61K 31/4164;
(Continued)

(56) References Cited

U.S. PATENT DOCUMENTS

| 5,223,409 A | 6/1993 | Ladner et al. |
| 2003/0170765 A1 | 9/2003 | Rouhani et al. |

(Continued)

FOREIGN PATENT DOCUMENTS

| CN | 10115767 A | * 4/2008 |
| WO | WO 92/20646 | 11/1992 |

(Continued)

OTHER PUBLICATIONS

Brycki et al. (Polish Journal of Microbiology 2010;59(1):49-53) (Year: 2010).*

(Continued)

*Primary Examiner* — Ernst V Arnold
(74) *Attorney, Agent, or Firm* — Casimir Jones, S.C.; Jason R. Bond

(57) ABSTRACT

Provided herein are compositions, systems, and methods for treating a disease, such as kidney and/or cardiovascular disease, with an agent that reduces the production of trimethylamine (TMA) or trimethylamine-n-oxide (TMAO) in a subject. In certain embodiments, the agent is: i) 3,3-dimethyl-1-butanol (DMB) or a DMB derivative or related compound, ii) acetylsalicylic acid or derivative thereof (e.g., with an enteric coating for delivery to the colon and/or cecum); iii) a flavin monooxygenase 3 (FMO3) inhibitor; iv) a gut TMA lyase inhibitor; v) an antibiotic or antimicrobial; vi) a probiotic or prebiotic; vii) an antiplatelet agent; or viii) a TMA and/or TMAO sequestering agent.

13 Claims, 15 Drawing Sheets

Specification includes a Sequence Listing.

Related U.S. Application Data

(60) Provisional application No. 62/056,168, filed on Sep. 26, 2014.

(51) Int. Cl.

| | |
|---|---|
| G01N 33/49 | (2006.01) |
| A61K 31/13 | (2006.01) |
| A61K 31/133 | (2006.01) |
| A61K 31/205 | (2006.01) |
| A61K 31/4164 | (2006.01) |
| A61K 31/43 | (2006.01) |
| A61K 31/4365 | (2006.01) |
| A61K 31/4709 | (2006.01) |
| A61K 31/496 | (2006.01) |
| A61K 31/519 | (2006.01) |
| A61K 31/675 | (2006.01) |
| A61P 9/00 | (2006.01) |
| A61P 13/12 | (2006.01) |

(52) U.S. Cl.
CPC ........ *A61K 31/205* (2013.01); *A61K 31/4164* (2013.01); *A61K 31/43* (2013.01); *A61K 31/4365* (2013.01); *A61K 31/4709* (2013.01); *A61K 31/496* (2013.01); *A61K 31/519* (2013.01); *A61K 31/675* (2013.01); *A61P 9/00* (2018.01); *A61P 13/12* (2018.01); *G01N 33/492* (2013.01); *G01N 2800/32* (2013.01); *G01N 2800/34* (2013.01); *G01N 2800/52* (2013.01)

(58) Field of Classification Search
CPC ................ A61K 31/43; A61K 31/4365; A61K 31/4709; A61K 31/496; A61K 31/519; A61K 31/616; A61K 31/675; A61P 13/12; A61P 9/00; G01N 2800/32; G01N 2800/34; G01N 2800/52; G01N 33/492
See application file for complete search history.

(56) References Cited

U.S. PATENT DOCUMENTS

| | | |
|---|---|---|
| 2012/0207822 A1 | 8/2012 | Hazen et al. |
| 2013/0345171 A1 | 12/2013 | Hazen et al. |
| 2014/0271923 A1 | 9/2014 | Reid |
| 2016/0089386 A1 | 3/2016 | Hazen |
| 2016/0089387 A1 | 3/2016 | Hazen |

FOREIGN PATENT DOCUMENTS

| | | |
|---|---|---|
| WO | WO 01/82864 | 4/2001 |
| WO | WO 2014/064630 | 5/2014 |
| WO | WO 2016/049537 | 3/2016 |
| WO | WO 2016/049541 | 3/2016 |

OTHER PUBLICATIONS

Scifinder CN 101157667A Apr. 2008 2 pages. (Year: 2008).*
Al-Waiz et al., The metabolism of 14C-labelled trimethylamine and its N-oxide in man. Xenobiotica 1987; 17(5):551-8.
Anders et al., The intestinal microbiota, a leaky gut, and abnormal immunity in kidney disease, Kidney Int 2013; 83(6):1010-6.
Bain et al., Accumulation of trimethylamine and trimethylamine-N-oxide in end-stage renal disease patients undergoing haemodialysis. Nephrol Dial Transplant 2006; 21(5):1300-4.
Bain et al., Oral L-carnitine: metabolite formation and hemodialysis. Curr Drug Metab 2006;7(7):811-6.
Barlow et al., The effects of inhibiting choline dehydrogenase on choline metabolism in mice. Biochem Pharmacol. Sep. 1, 1985;34(17):3117-22.
Bell et al., Nuclear magnetic resonance studies of blood plasma and urine from subjects with chronic renal failure: identification of trimethylamine-N-oxide. Biochim Biophys Acta 1991;1096(2):101-7.
Bennett et al.; Trimethylamine-Noxide, a metabolite associated with atherosclerosis, exhibits complex genetic and dietary regulation; Cell Metab 2013; 17(1):49-60.
Carell et al., A Solution-Phase Screening Procedure for the Isolation of Active Compounds from a Library of Molecules, Angew. Chem. Int. Ed. Engl. 33:2061-2064 (1994).
Carell et al., A Novel Procedure for the Synthesis of Libraries Containing Small Organic Molecules, Angew. Chem. Int. Ed. Engl., 33:2059-2061 (1994).
Carlsson et al., Urinary kidney injury molecule 1 and incidence of heart failure in elderly men. Eur J Heart Fail. Apr. 2013;15(4):441-6.
Cho et al., An unnatural biopolymer, Science, (1993); 261:1303.
Craciun et al., Microbial conversion of choline to trimethylamine requires a glycyl radical enzyme, PNAS, 2012, 109:21307-21312.
Cull et al., Screening for receptor ligands using large libraries of peptides linked to the C terminus of the lac repressor, Proc. Nad. Acad. Sci. USA, 1992; 89:1865-1869.
Cwirla et al., Peptides on phage: a vast library of peptides for identifying ligands, Proc. Natl. Acad. Sci., (1990); 87:6378-6382.
Devlin et al., Random peptide libraries: a source of specific protein binding molecules, Science, (1990); 249:404-406.
DeWitt et al., "Diversomers": an approach to nonpeptide, nonoligomeric chemical diversity, Proc. Natl. Acad. Sci. U.S.A. (1993); 90:6909-6913.
eMedicinehealth, Chronic Kidney Disease, http://www.emedicinehealth.com/script/main/art.asp?articlekey=58887&pf=2, retrieved Sep. 24, 2016, 10 pages.
eMedicinehealth, Congestive Heart Failure, http://emedicinehealth.com/script/main/art.asp?articlekey=58674&pf=2, retrieved Sep. 24, 2016, 11 pages.
Erb et al., Recursive deconvolution of combinatorial chemical libraries, Proc. Nad. Acad. Sci. USA, (1994); 91:11422-11426.
Felici et al., Selection of antibody ligands from a large library of oligopeptides expressed on a multivalent exposition vector, J. Mol. Biol., 1991; 222:301-310.
Fodor et al., Multiplexed biochemical assays with biological chips, Nature, 1993; 364:555-556.
Foxall et al., NMR spectroscopy as a novel approach to the monitoring of renal transplant function. Kidney Int. 1993;43(1):234-45.
Gallop et al., Applications of combinatorial technologies to drug discovery. 1. Background and peptide combinatorial libraries, J Med Chem. Apr. 29, 1994;37(9):1233-51.
Gogonea et al., Congruency between biophysical data from multiple platforms and molecular dynamics simulation of the double-super helix model of nascent high-density lipoprotein, Biochemistry. Aug. 31, 2010;49(34):7323-43.
Hauet et al., Proton NMR spectroscopy as a novel approach to the monitoring of citrate and trimethylamine-N-oxide excretion after kidney preservation. Transplant Proc. Aug. 1997;29(5):2323-5.
Hegazy et al., Effect of probiotics on pro-inflammatory cytokines and NF-kappaB activation in ulcerative colitis. World J Gastroenterol 2010;16(33):4145-51.
Houghten et al., The use of synthetic peptide combinatorial libraries for the identification of bioactive peptides, Biotechniques. Sep. 1992;13(3):412-21.
Inker et al., Estimating glomerular filtration rate from serum creatinine and cystatin C. N Engl J Med. Jul. 5, 2012;367(1):20-9.
Khella et al., Stroke and its prevention in chronic kidney disease. Clin J Am Soc Nephrol. Nov. 2007;2(6):1343-51.
Koenig et al., Plasma concentrations of cystatin C in patients with coronary heart disease and risk for secondary cardiovascular events: more than simply a marker of glomerular filtration rate. Clin Chem. Feb. 2005;51(2):321-7.
Koeth et al., gamma-Butyrobetaine is a proatherogenic intermediate in gut microbial metabolism of L-carnitine to TMAO, Cell Metab., 2014 20:799-812.

(56) References Cited

OTHER PUBLICATIONS

Koeth et al., Intestinal microbiota metabolism of L-carnitine, a nutrient in red meat, promotes atherosclerosis. Nat Med 2013;19(5):576-85.
Lam, Application of combinatorial library methods in cancer research and drug discovery, Anticancer Drug Des. Apr. 1997;12(3):145-6.
Lam et al., A new type of synthetic peptide library for identifying ligand-binding activity,Nature. Nov. 7, 1991;354(6348):82-4.
Le Moyec et al., Proton nuclear magnetic resonance spectroscopy of urine and plasma in renal transplantation follow-up, Nephron 1993;65(3):433-9.
Lee et al., Effects of AST-120 on blood concentrations of protein-bound uremic toxins and biomarkers of cardiovascular risk in chronic dialysis patients. Blood Purif 2014;37(1):76-83.
Lekawanvijit et al., Cardiorenal syndrome: the emerging role of protein-bound uremic toxins. Circ Res 2012;111(11):1470-83.
Lin et al., Associations of diet with albuminuria and kidney function decline. Clin J Am Soc Nephrol 2010;5(5):836-43.
Mafra et al., Role of altered intestinal microbiota in systemic inflammation and cardiovascular disease in chronic kidney disease. Future Microbiol 2014;9:399-410.
MedlinePlus, Medical Encylclopedia: Typ 1 diabetes, http://www.nih.gov/medlineplus/print/ency/article/000305.htm, retrieved Jun. 11, 2009, 7 pages.
Mistry et al., Neurochemistry of aging. 2. Design, synthesis, and biological evaluation of halomethyl analogues of choline with high affinity choline transport inhibitory activity. J Med Chem. Jul. 1991;34(7):2031-6.
Niwa et al., Indoxyl sulfate, a circulating uremic toxin, stimulates the progression of glomerular sclerosis. J Lab Clin Med 1994;124(1):96-104.
Palmer et al., Antiplatelet Agents for Chronic Kidney Disease, The Cochrane Library, 2013, Issue 2, 99 pages.
Pencina et al., Evaluating the added predictive ability of a new marker: from area under the ROC curve to reclassification and beyond. Stat Med 2008;27(2):157-72; discussion 207-12.
Qu et al., Regulation of renal fibrosis by Smad3 thr388 phosphorylation. Am J Pathol 2014;184(4):944-52.
Ramezani et al., The gut microbiome, kidney disease, and targeted interventions, J Am Soc Nephrol 2014;25(4):657-70.
Ranganathan et al., Pilot study of probiotic dietary supplementation for promoting healthy kidney function in patients with chronic kidney disease. Adv Ther 2010;27(9):634-47.
Ranganathan et al., Probiotic amelioration of azotemia in 5/6th nephrectomized Sprague—Dawley rats. ScientificWorldJournal 2005;5:652-60.
Rhee et al., A combined epidemiologic and metabolomic approach improves CKD prediction. J Am Soc Nephrol 2013;24(8):1330-8.
Robert et al., A pair analysis of the delayed graft function in kidney recipient: the critical role of the donor. Journal of critical care 2010;25(4):582-90.
Rossi et al., Synbiotics Easing Renal Failure by improving Gut microbiologY (SYNERGY): a protocol of placebo-controlled randomised cross-over trial, BMC Nephrology, 2014, 15:106, 10 pages.
Runyan et al., Smad3 and PKCdelta mediate TGF-beta1-induced collagen I expression in human mesangial cells. Am J Physiol Renal Physiol 2003; 285(3):F413-22.
Scott et al., Searching for peptide ligands with an epitope library,Science. Jul. 27, 1990;249(4967):386-90.
Sekowska et al., Sulfur Metabolism in *Escherichia coli* and Related Bacteria: Facts and Fiction, J Mol Microbiol Biotechnol., 2000, 2:145-177.
Serkova et al., H-NMR-based metabolic signatures of mild and severe ischemia/reperfusion injury in rat kidney transplants. Kidney Int 2005;67(3):1142-51.

Seth et al., Probiotics ameliorate the hydrogen peroxideinduced epithelial barrier disruption by a PKC- and MAP kinase-dependent mechanism. Am J Physiol Gastrointest Liver Physiol 2008;294(4):G1060-9.
Shephard et al., Clinical utility gene card for: Trimethylaminuria, Eur J Hum Genetics, 2012, 20, doi:10.1038/ejhg.2011.214, 5 pages.
Simenhoff et al., Biomodulation of the toxic and nutritional effects of small bowel bacterial overgrowth in end-stage kidney disease using freeze-dried Lactobacillus acidophilus. Miner Electrolyte Metab 1996;22(1-3):92-6.
Smith et al., Metabolism and excretion of methylamines in rats. Toxicol Appl Pharmacol 1994;125(2):296-308.
Stenvinkel et al., Inflammation in end-stage renal disease: sources, consequences, and therapy. Semin Dial 2002;15(5):329-37.
Takayama et al., Bifidobacterium in gastro-resistant seamless capsule reduces serum levels of indoxyl sulfate in patients on hemodialysis. Am J Kidney Dis 2003;41(3 Suppl 1):S142-5.
Tang et al., Gut microbiota-dependent trimethylamine N-oxide (TMAO) pathway contributes to both development of renal insufficiency and mortality risk in chronic kidney disease, Circ. Res, 2015, 116:448-55.
Tang et al., Intestinal microbial metabolism of phosphatidylcholine and cardiovascular risk. N Engl J Med 2013;368(17):1575-84.
Tang et al., Intestinal microbiota-dependent phosphatidylcholine metabolites, diastolic dysfunction, and adverse clinical outcomes in chronic systolic heart failure, J Card Fail., 2015, 21:91-6.
Tang et al., Prognostic value of elevated levels of intestinal microbe-generated metabolite trimethylamine-N-oxide in patients with heart failure: refining the gut hypothesis; J Am Coll Cardiol, 2014, 64: 1908-14.
Vaziri et al., Chronic kidney disease alters intestinal microbial flora. Kidney Int 2013;83(2):308-15.
Vigil et al., Cystatin C as a predictor of mortality and cardiovascular events in a population with chronic kidney disease. Int J Nephrol. 2014;2014:127943.
Wang et al., Gut flora metabolism of phosphatidylcholine promotes cardiovascular disease. Nature 2011;472(7341):57-63.
Wang et al., Measurement of trimethylamine-N-oxide by stable isotope dilution liquid chromatography tandem mass spectrometry. Anal Biochem 2014;455:35-40.
Wang et al., Prognostic value of choline and betaine depends on intestinal microbiotagenerated metabolite trimethylamine-N-oxide. Eur Heart J 2014;35(14):904-10.
Wang et al., Non-lethal Inhibition of Gut Microbial Trimethylamine Production for the Treatment of Atherosclerosis. Cell. Dec. 17, 2015;163(7):1585-95.
Williams et al., Optimizing clinical use of mesalazine (5-aminosalicylic acid) in inflammatory bowel disease, Therap Adv Gastroenterol., 2011, 4(4): 237-248.
Wu, Diet, the Gut Microbiome and the Metabiolome in IBD, Nutrition, Gut Microbiota and Immunity Theraputic Tagets IBD, 2014, 79:78.
Zeisel et al., Conversion of dietary choline to trimethylamine and dimethylamine in rats: dose-response relationship. J Nutr 1989;119(5):800-4.
Zuckermann et al.,Discovery of nanomolar ligands for 7-transmembrane G-protein-coupled receptors from a diverse N-(substituted)glycine peptoid library,J Med Chem.Aug. 19, 1994;37(17):2678-8.
International Search Report and Written Opinion for PCT/US2015/052380, dated Apr. 21, 2016, 15 pages.
International Search Report and Written Opinion for PCT/US2015/052372, dated Feb. 26, 2016, 14 pages.
Extended European Search Report for EP15843415.9, dated Mar. 5, 2018, 9 pages.

\* cited by examiner

FIG. 10 yeaW

GeneID|6060925|ref|NC_010473.1|1973260-1974384 Escherichia coli str. K-12 substr. DH10B (SEQ ID NO:1)

ATGAGCAATCTGAGCCCTGACTTTGTACTACCCGAAAATTTTTGCGCTAACCCGCAAGAGGCGTGGACCA
TTCCTGCCCGTTTTTATACCGATCAGAACGCGTTTGAACACGAAAAAGAGAACGTCTTCGCCAAAAGCTG
GATTTGCGTCGCTCACAGCAGCGAACTGGCGAATGCCAATGATTATGTGACGCGTGAGATCATTGGCGAA
AGCATCGTGCTGGTACGCGGTCGTGATAAGGTTTTGCGCGCGTTCTATAACGTGTGTCCGCACCGTGGTC
ATCAGTTGTTGAGCGGTGAAGGAAAAGCAAAAAATGTGATTACCTGCCCGTATCACGCATGGGCATTCAA
ACTCGATGGCAACCTGGCCCATGCACGTAACTGCGAAAACGTCGCCAATTTCGATAGCGACAAAGCGCAA
CTGGTTCCGGTGCGTCTGGAAGAATATGCCGGATTCGTCTTCATCAACATGGACCCCAACGCCACCAGCG
TAGAAGATCAATTACCCGGCCTGGGCGCGAAAGTGCTGGAAGCCTGCCCGGAAGTCCACGATCTGAAACT
GGCGGCCCGCTTTACCACCCGCACGCCTGCCAACTGGAAGAACATTGTCGATAACTATCTCGAGTGCTAT
CACTGTGGTCCGGCGCATCCAGGTTTCTCCGACTCCGTACAGGTTGATCGTTACTGGCACACCATGCACG
GTAACTGGACGCTGCAATACGGTTTCGCCAAACCGTCCGAACAGTCGTTTAAATTTGAAGAGGGTACGGA
TGCGGCATTCCACGGTTTCTGGCTGTGGCCGTGCACGATGCTGAACGTCACCCCGATCAAAGGGATGATG
ACGGTCATTTATGAATTCCCGGTGGATTCTGAAACTACCCTGCAAAACTACGATATTTACTTCACCAATG
AAGAGTTAACCGACGAGCAAAAATCGCTGATTGAGTGGTATCGCGATGTGTTCCGTCCGGAAGATTTACG
TCTGGTTGAAAGCGTACAGAAAGGGCTGAAATCGCGTGGCTATCGTGGTCAGGGGCGCATCATGGCCGAC
AGTAGCGGTAGTGGCATTTCCGAACATGGTATCGCCCATTTCCATAATCTGCTGGCGCAGGTGTTTAAGG
ACTAA (SEQ ID NO:2)

MSNLSPDFVLPENFCANPQEAWTIPARFYTDQNAFEHEKENVFAKSWICVAHSSELANANDYVTREIIGE
SIVLVRGRDKVLRAFYNVCPHRGHQLLSGEGKAKNVITCPYHAWAFKLDGNLAHARNCENVANFDSDKAQ
LVPVRLEEYAGFVFINMDPNATSVEDQLPGLGAKVLEACPEVHDLKLAARFTTRTPANWKNIVDNYLECY
HCGPAHPGFSDSVQVDRYWHTMHGNWTLQYGFAKPSEQSFKFEEGTDAAFHGFWLWPCTMLNVTPIKGMM
TVIYEFPVDSETTLQNYDIYFTNEELTDEQKSLIEWYRDVFRPEDLRLVESVQKGLKSRGYRGQGRIMAD
SSGSGISEHGIAHFHNLLAQVFKD

FIG. 11 yeaX

GeneID|6060982|ref|NC_010473.1|1974440-1975405 Escherichia coli str. K-12 substr. DH10B (SEQ ID NO:3)

ATGTCAGACTATCAAATGTTTGAAGTACAGGTGAGCCAGGTTGAACCCCTTACCGAACAGGTGAAACGCT
TCACGCTGGTGGCAACCGATGGCAAACCATTACCTGCGTTTACCGGAGGAAGTCACGTCATTGTGCAGAT
GAGCGATGGTGATAACCAGTACAGCAATGCGTATTCACTACTGAGTTCGCCGCATGACACCTCTTGTTAT
CAGATTGCCGTTCGGCTGGAGGAAAACTCGCGCGGCGGTTCCCGCTTTTTGCATCAGCAGGTAAAAGTGG
GCGATCGGTTAACGATTTCAACGCCTAATAACCTGTTTGCGCTAATTCCCTCAGCCAGAAAGCATCTGTT
TATCGCGGGCGGTATTGGTATCACCCCTTTCCTGTCGCACATGGCAGAGCTGCAACACAGCGACGTCGAC
TGGCAGCTACATTACTGCTCGCGAAATCCAGAAAGTTGCGCATTTCGTGATGAGCTAGTCCAGCATCCGC
AGGCTGAGAAAGTCCATTTGCATCATTCATCAACCGGAACACGACTGGAATTAGCGCGATTATTGGCGGA
TATCGAACCTGGCACACACGTTTATACCTGTGGCCCCGAGGCGCTAATTGAAGCGGTAAGAAGTGAAGCT
GCGCGTCTGGACATCGCCGCCGATACGCTGCACTTTGAGCAATTTGCTATCGAAGACAAAACCGGCGATG
CATTTACCCTGGTGCTTGCCCGTTCCGGAAAAGAGTTTGTGGTGCCGGAAGAGATGACTATTTTGCAGGT
TATTGAAAATAATAAAGCCGCGAAAGTGGAATGTTTATGTCGTGAAGGGGTATGCGGAACCTGCGAAACA
GCAATACTGGAAGGTGAAGCTGACCATCGGGATCAATATTTTAGCGATGAAGAGCGTGCCAGCCAGCAAA
GTATGTTGATCTGTTGTTCGCGTGCGAAGGGTAAACGCCTGGTGTTGGATTTGTAG (SEQ ID NO:4)

MSDYQMFEVQVSQVEPLTEQVKRFTLVATDGKPLPAFTGGSHVIVQMSDGDNQYSNAYSLLSSPHDTSCY
QIAVRLEENSRGGSRFLHQQVKVGDRLTISTPNNLFALIPSARKHLFIAGGIGITPFLSHMAELQHSDVD
WQLHYCSRNPESCAFRDELVQHPQAEKVHLHHSSTGTRLELARLLADIEPGTHVYTCGPEALIEAVRSEA
ARLDIAADTLHFEQFAIEDKTGDAFTLVLARSGKEFVVPEEMTILQVIENNKAAKVECLCREGVCGTCET
AILEGEADHRDQYFSDEERASQQSMLICCSRAKGKRLVLDL

TREATING AND PREVENTING DISEASE WITH TMA AND TMAO LOWERING AGENTS

CROSS-REFERENCE TO RELATED APPLICATIONS

The present invention is a continuation of U.S. patent application Ser. No. 14/866,398, filed Sep. 25, 2015, which claims priority to U.S. Provisional Patent Application 62/056,168, filed Sep. 26, 2014, each of which is incorporated by reference in its entirety.

FIELD OF THE INVENTION

Provided herein are compositions, systems, and methods for treating a disease, such as kidney disease and/or cardiovascular disease, with an agent that reduces the production of trimethylamine (TMA) or trimethylamine-n-oxide (TMAO) in a subject. In certain embodiments, the agent is: i) 3,3-dimethyl-1-butanol (DMB) or a DMB derivative or related compound, ii) acetylsalicylic acid or derivative thereof (e.g., with an enteric coating for delivery to the colon and/or cecum); iii) a flavin monooxygenase 3 (FMO3) inhibitor; iv) a gut TMA lyase inhibitor; v) an antibiotic or antimicrobial; vi) a probiotic or prebiotic; vii) an antiplatelet agent, or vii) a TMA and/or TMAO sequestering agent.

BACKGROUND

Kidneys of the human body function to remove excess fluids as well as some ions. The functional unit of the kidney is the nephron. A nephron consists of a filtering unit of tiny blood vessels called a glomerulus attached to a tubule. When blood enters the glomerulus, it is filtered and the remaining fluid then passes along the tubule. In the tubule, chemicals and water are either added to or removed from this filtered fluid according to the body's needs, and the final product is urine, which is excreted.

In patients with chronic kidney disease, kidney function is severely compromised. Chronic kidney disease (CKD), also known as chronic renal disease, is a progressive loss in renal function over a period of months or years. The most severe stage of CKD is End Stage Renal Disease (ESRD), which occurs when the kidneys cease to function. The two main causes of CKD are diabetes and high blood pressure, which are responsible for up to two-thirds of the cases. Heart disease is the leading cause of death for all people having CKD. Excessive fluid can accumulate in patients suffering from ESRD. The mortality rate of ESRD patients who receive traditional hemodialysis therapy is 24% per year with an even higher mortality rate among diabetic patients. Fluid accumulates in ESRD patients because the kidneys can no longer effectively remove water and other fluids from the body. The fluid accumulates first in the blood and then accumulates throughout the body, resulting in swelling of the extremities and other tissues as edema. This accumulation of fluid causes increased stress on the heart, in turn causing significant increases in blood pressure or hypertension, which can lead to heart failure.

Although the population of patients afflicted with CKD grows each year, there is no cure. Current treatments for CKD seek to slow the progression of the disease. However, as the disease progresses, renal function decreases, and, eventually, renal replacement therapy is employed to compensate for lost kidney function. Renal replacement therapy entails either transplantation of a new kidney or dialysis.

Methods to treat kidney disease require the processing of blood to extract waste components such as urea and ions. The traditional treatment for kidney disease involves dialysis. Dialysis emulates kidney function by removing waste components and excess fluid from a patient's blood. This is accomplished by allowing the body fluids, usually the blood, to come into the close proximity with the dialysate, which is a fluid that serves to cleanse the blood and actively remove the waste components and excess water. During this process, the blood and dialysate are separated by a dialysis membrane, which is permeable to water, small molecules (such as urea), and ions but not permeable to the cells. Each dialysis session lasts a few hours and may be repeated as often as three times a week.

Traditional processes, such as dialysis, require extracorporeal processing of body fluids. Once the blood is purified, it is then returned to the patient. Although effective at removing waste components from blood, dialysis treatments are administered intermittently and, therefore, do not emulate the continuous function of a natural kidney. Once the dialysis session is completed, the fluid begins to accumulate again in the tissues of the patient. The benefits of dialysis notwithstanding, statistics indicate that three out of five dialysis patients die within five years of commencing treatment. Studies have shown that increasing the frequency and duration of dialysis sessions can improve the survivability of dialysis patients. Increasing the frequency and duration of dialysis sessions more closely resembles the continuous kidney function sought to be emulated. However, the extracorporeal processing of the body fluids increases the discomfort, inconvenience and the costs associated with treatment. There is also an additional risk of infection, which mandates that the procedures be carried out under the supervision of trained medical personnel.

SUMMARY OF THE INVENTION

Provided herein are compositions, systems, and methods for treating a disease, such as kidney disease, or cardiovascular disease, with an agent that reduces the production of trimethylamine (TMA) or trimethylamine-n-oxide (TMAO) in a subject. In certain embodiments, the agent is: i) 3,3-dimethyl-1-butanol (DMB) or a DMB derivative or related compound, ii) acetylsalicylic acid or derivative thereof (e.g., with an enteric coating for delivery to the colon and/or cecum); iii) a flavin monooxygenase 3 (FMO3) inhibitor; iv) a gut TMA lyase inhibitor; v) an antibiotic or antimicrobial; vi) a probiotic or prebiotic; vii) an antiplatelet agent; vii) a TMA and/or TMAO sequestering agent.

In some embodiments, provided herein are methods of treating or preventing kidney disease, and/or cardiovascular disease, comprising: treating a subject with an agent or procedure (or prescribing or recommending treating with an agent or procedure), wherein: i) the subject has symptoms of kidney disease, and/or cardiovascular disease, and the treating reduces or eliminates at least one symptom of the kidney and/or cardiovascular disease; ii) the subject is apparently healthy, but has elevated levels of TMAO, and the treating prevents the development of chronic kidney and/or cardiovascular disease in the subject; or iii) the subject has age-related decline in kidney function, and the treating prevents or attenuates further decline in the kidney function; and iv) said the or procedure is selected from: a) 3,3-dimethyl-1-butanol (DMB) or a DMB derivative or related compound (e.g., as shown in Table 3); b) acetylsalicylic acid with or without an enteric coating; c) an acetylsalicylic acid derivative with or without an enteric coating; d) a flavin monooxygenase 3 (FMO3) inhibitor; e) a gut TMA lyase inhibitor; f) fecal microbiota transplantation; g) delivery of acetylsalicylic acid or derivative thereof directly to the colon or cecum of the subject; h) an antibiotic or antimicrobial that reduces trimethylamine (TMA) production in the gut; i) a probiotic or prebiotic that reduces TMA production in the gut; j) an antiplatelet agent; and k) a TMA and/or TMAO sequestering agent. In certain embodiments, a subject is treated prophylactically with the agents and procedures mentioned herein to promote renal health and prevent TMAO induced impairment of renal function.

In particular embodiments, rather than, or in addition to treating, the patient is prescribed one of the agents or procedures described herein. In some embodiments, a patient with kidney and/or cardiovascular disease is also, or alternatively, prescribed a diet with reduced levels of carnitine containing compounds (e.g., prescribed a vegetarian or vegan diet). In certain embodiments, the diet is a Mediterranean diet, or diet low in TMAO precursors (e.g., low in choline, lecithin, carnitine, etc.), or low in TMAO (e.g., a diet low in certain fish, such as cod, tilapia, Chilean sea bass, etc.).

In certain embodiments, a sample from the subject is assayed to determine levels of eGFR, eCrCl, Cystatin C, KIM1, microalbuniuria (an elevated urine albumin/Creatinine ratio), trimethylamine N-oxide (TMAO), TMA, and/or a TMA-containing compound prior to and/or after said treating. In particular embodiments, a subject is found to need treatment if elevated levels of KIM1, TMA, TMAO, or elevated urine albumin/Creatine ratio are found. In other embodiments, a subject is found to need treatment if decreased levels of eFGF, eCrCl, or increased Cystatin C are found. In other embodiments, the sample comprises whole blood, serum, plasma, exhaled breath, urine, saliva, cerebrospinal fluid, or bronchoalveolar lavage.

In other embodiments, the DMB derivative or related compound is as shown in Formula I below:

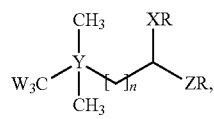

wherein n is an integer, or n is 0, indicating that $CH_2$ is not present;
wherein each W is independently selected from: H, Cl, F, Br, or I (e.g., $W_3C=CH_3$, $CH_2Cl$, $CH_2Fl$, $CH_2Br$, $CH_2I$, $CF_3$, $CCl_3$, $CBr_3$, $CI_3$, or $CHCl_2$);
wherein Y is C, N, Si, P, S, Ge, Sn, Pb, P, As, Sb, or Bi;
wherein X is O or S and the corresponding bond is either present or absent or double,
wherein R is absent, H, an alkyl group, alkenyl group, alkynyl group, phenyl group, amide, alkylamide, or a benzyl group;
wherein Z is C, $CH_2$, CH, NH, O, or S,
wherein XR is, alternatively, H, an ester, thioester, or thionester; glycerol, or one of the following three formulas:

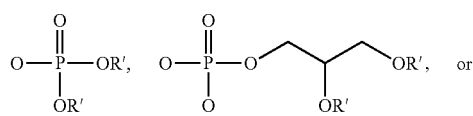

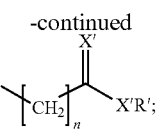

wherein R' is H, an alkyl group, alkenyl group, alkynyl group, phenyl group, or a benzyl group; and wherein X' is O, or S. In certain embodiments, R is amide or alkylamide, and Z is an O, and Z as a double bond O—a carboxylic acid). In some embodiments, the two methyl groups extending from Y are linked by an alkyl or ether to form a 4-6 member ring.

In further embodiments, the acetylsalicylic acid derivative or related compound is selected from the group consisting of: 4-Methylsalicylic acid, 5-(acetylamino)-2-hydroxybenzoic acid; Salicylic acid, sodium salt, 4-Aminosalicylic acid, 3-Methylsalicylic acid, 3-Nitrosalicylic acid, 1-Hydroxy-2-naphthoic acid, 2-Hydroxyethyl salicylate, 5-Bromosalicylic acid, 5-Methylsalicylic acid, 5-Aminosalicylic acid, 2,4-Dihydroxybenzoic acid, 2,4-Dimethoxybenzoic acid, 3-Hydroxy-2-naphthoic acid, 5-Nitrosalicylic acid, Phenyl salicylate, Ethyl salicylate, 5-Iodosalicylic acid, Methyl salicylate, 5,5'-Methylenedisalicylic acid, Pamoic acid, 2-Ethoxybenzoic acid, 2,6-Dihydroxybenzoic acid, 2,3-Dihydroxybenzoic acid, Ochratoxin A, 5-Chlorosalicylic acid, 4-Fluorosalicylic acid, Methyl 5-fluoro-2-hydroxybenzoate, 2,4,5-Trimethoxybenzoic acid, 2,5-Dihydroxybenzoic acid, Acetyl salicyl salicylic acid, Salicyl salicylic acid, 6-Methyl salicylic acid, Aluminon, 3-Aminosalicylic acid, 2,3,4-Trimethoxybenzoic acid, o-Anisic acid, Isopropyl salicylate, 3,5-Dinitrosalicylic acid, 2,3,4-Trihydroxybenzoic acid, 5-Formylsalicylic acid, 2-Hydroxy-4-nitrobenzoic acid, Lithium 3,5-diiodosalicylate, 4-Fluorosulfonyl-1-hydroxy-2-naphthoic acid, 3-Methoxysalicylic acid, Methyl 1-hydroxy-2-naphthoate, Carminic acid, Carmine (pure, alum lake of carminic acid), Carmine (high purity biol.stain, alum lake of carminic acid), 2,6-Dimethoxybenzoic acid, 2,3-Dimethoxybenzoic acid, Chrome Azurol S, Alizarin Yellow R sodium salt, 3-Chlorosalicylic acid, 2-(trifluoromethoxy) benzoic acid, Methyl 2,4-dimethoxybenzoate, Methyl 2,6-dihydroxybenzoate, Methyl 2,4-dihydroxybenzoate, Triethanolamine salicylate, 2-Ethoxynaphthoic acid, 4-Methoxysalicylic acid, 5-Methoxysalicylic acid, 2,5-Dimethoxybenzoic acid, 3,5 Dibromosalicylic acid, 6-Methoxysalicylic acid, 5-Chloro-o-anisic acid, Chromoxane Cyanine R, 3-Hydroxy-4-(2-hydroxy-4-sulfo-1-naphthylazo) naphthalene-2-carboxylic acid, indicator grade ethyl 2,3-dihydroxybenzoate, Methyl 5-iodosalicylate, methyl 5-chloro-2-hydroxybenzoate, Methyl 4-acetamido-5-chloro-2-methoxybenzoate, 2-(acetyloxy)-3-methylbenzoic acid, 2-(acetyloxy)-3-methylbenzoic acid, 1,4-Benzodioxan-5-carboxylic acid, 2-Methoxy-5-(trifluoromethyl)benzoic acid, 4-Chlorosalicylic acid, Methyl 4-methoxysalicylate, 1,3-benzodioxole-4-carboxylic acid, 5-Sulfosalicylic acid dihydrate, 5-Sulfosalicylic acid dihydrate, 5-Sulfosalicylic acid dihydrate, Mordant Yellow 10, 4-Amino-5-chloro-2-methoxybenzoic acid, Methyl 5-acetylsalicylate, 5-chlorosulfonyl-2-hydroxybenzoic acid, methyl 2-[2-(dimethylamino)ethoxy]benzoate, alpha-Apo-oxytetracycline, beta-Apo-oxytetracycline, 3,5-Di-tert-butylsalicylic acid, Methyl 3,5-dibromo-2-hydroxybenzoate, 2-(3-methoxyphenoxy) benzoic acid, Methyl 3-nitrosalicylate, Methyl 5-methyl salicylate, methyl 4-amino-2-methoxybenzoate, chroman-8-carboxylic acid, methyl 2,5-di(2,2,2-trifluoroethoxy)benzoate, 2,3 dihydrobenzo[b]furan-7-carboxylic acid, methyl 3-amino-2-hydroxybenzoate, 3-chloro-2,6-dimethoxybenzoic acid, 3-Hydroxyphthalic anhydride, 5-Bromo-2,3-dihydrobenzo[b]furan-7-carboxylic Acid, 2,2-dimethyl-2,3-dihydro-1-benzofuran-7-carboxylic acid, 6-Fluorosalicylic acid, 2,4,6-Trihydroxybenzoic acid monohydrate, 3-bromo-2,6-dimethoxybenzoic acid, 3-bromo-2,6-dimethoxybenzoic acid, 3,5-dichloro-2,6-dimethoxybenzoic acid, Lavendustin A, 2-Fluoro-6-methoxybenzoic acid, 5-Bromo-2,4-dihydroxybenzoic acid monohydrate, 3-chloro-2,6-dimethoxy-5-nitrobenzoic acid, methyl 4,7-dibromo-3-methoxy-2-naphthoate, 2-(trifluoromethoxy)terephthalic acid, 2-methoxy-4,6-di(trifluoromethyl)benzoic acid, 2-[2-(dimethylamino)ethoxy]benzoic acid, 2-[(5-chloro-3-pyridyl)oxy]-5-nitrobenzoic acid, 6-fluoro-4H-1,3-benzodioxine-8-carboxylic acid, 3-Methoxy-4-(methoxycarbonyl) phenylboronic acid pinacol ester, 3-Methoxy-4-(methoxycarbonyl)phenylboronic acid, 2-(tetrahydropyran-4-yloxy)benzoic acid, pentafluorophenyl 2-(tetrahydro-2H-pyran-4-yloxy)benzoate, 3-Hydroxy-4-(methoxycarbonyl) phenylboronic acid pinacol ester, and 3-Formylsalicylic acid hydrate.

In particular embodiments, the FMO3 inhibitor comprises Tenofovir or Methimazole. In some embodiments, the antibiotic is a broad spectrum antibiotic. In further embodiments, the antibiotic is one antibiotic or a combination of antibiotics selected from the group consisting of: metronidazole, ciprofloxacin, and neomycin, amoxicillin. In particular embodiments, the antiplatelet agent is selected from the group consisting of: abciximab, dipyridamole/ASA, anagrelide, cilostazol, clopidogrel, dipyridamole, eptifabatide, prasugrel, ticagrelor, ticlopidine, tirofiban, and vorapaxar. In further embodiments, the enteric coating provides for release of a majority of the acetylsalicylic acid or the acetylsalicylic acid derivative in the colon or cecum of the subject.

In some embodiments, the TMA and/or TMAO sequestering agent comprises activated charcoal or copper chlorophyllin (e.g., activated charcoal at 750 mg 2×/day for 10 days, or copper chlorophyllin at 60 mg 3×/day after meals for 3 weeks).

In some embodiments, provided herein are systems comprising: a) a report for a patient with kidney and/or cardiovascular disease indicating that the patient has elevated levels of TMA or TMAO; and b) an agent for treating kidney and/or cardiovascular disease selected from: i) 3,3-dimethyl-1-butanol (DMB) or a DMB derivative or related compound (e.g., as shown in Table 3); ii) acetylsalicylic acid (aspirin) with or without an enteric coating; iii) an acetylsalicylic acid derivative with or without an enteric coating; iv) a flavin monooxygenase 3 (FMO3) inhibitor; v) a gut TMA lyase inhibitor; vi) fecal microbiota transplantation agents; vii) an antibiotic or antimicrobial that reduces TMA production in the gut; viii) a probiotic or prebiotic that reduces TMA production in the gut; ix) an antiplatelet agent, and x) a TMA and/or TMAO sequestering agent.

In certain embodiments, provided herein are methods for treating a disease associated with elevated TMA and/or trimethylamine N-oxide (TMAO levels) comprising: treating a subject with symptoms of a disease associated with elevated TMA and/or TMAO levels with an agent comprising acetylsalicylic acid or an acetylsalicylic acid derivative, wherein the treating is under condition such that a majority or all of the agent is delivered to the subject's colon and/or cecum, and wherein the treating results in at least one symptom of the disease being reduced or eliminated.

In certain embodiments, the disease is a cardiovascular disease (e.g., Coronary Heart Disease, Cor Pulmonale, Congenital Heart Defect, Cardiomyopathy, Myocardial Infarction, Congestive Heart Failure, Valvular Heart Disease, Arrhythmia, Peripheral Arterial Disease, Cerebrovascular Accident, and Rheumatic Heart Disease). In certain embodiments, the disease is kidney disease. In other embodiments, the agent comprises an enteric coating that provides for release of a majority of the agent in the colon and/or cecum. In further embodiments, a sample from the subject is assayed to determine levels of trimethylamine N-oxide (TMAO), TMA, and/or a TMA-containing compound prior to and/or after the treating.

In some embodiments, provided herein are systems comprising: a) a report for a patient with a disease associated with elevated levels of TMAO and/or TMA indicating that the patient has elevated levels of TMAO and/or TMA; and b) an agent for treating the disease, wherein the agent comprises acetylsalicylic acid or an acetylsalicylic acid derivative (e.g., with an enteric coating that allows for delivery to a subject's colon and/or cecum).

In other embodiments, provided herein are systems comprising: a) an agent comprising acetylsalicylic acid or an acetylsalicylic acid derivative; and b) equipment that allows delivery of the agent directly to the cecum and/or colon of a human subject.

In further embodiments, provided herein are methods for identifying TMA lyase inhibitors comprising: a) contacting a TMA-containing compound and a candidate inhibitor with a complex comprising the yeaW protein (e.g., from $E.\ coli$) and the yeaX protein (e.g., from $E.\ coli$) under conditions that the complex cleaves the TMA-containing compound if not inhibited by the candidate inhibitor; and b) determining if the complex cleaves the TMA-containing compound, wherein absence of cleavage identifies the candidate inhibitor as a TMA lyase inhibitor.

BRIEF DESCRIPTION OF THE FIGURES

FIG. 10 shows the nucleic acid sequence (SEQ ID NO:1) and amino acid sequence (SEQ ID NO:2) of the E. Coli yeaW gene and protein.

FIG. 11 shows the nucleic acid sequence (SEQ ID NO:3) and amino acid sequence (SEQ ID NO:4) of the E. Coli yeaX gene and protein.

DEFINITIONS

Figure 1B:
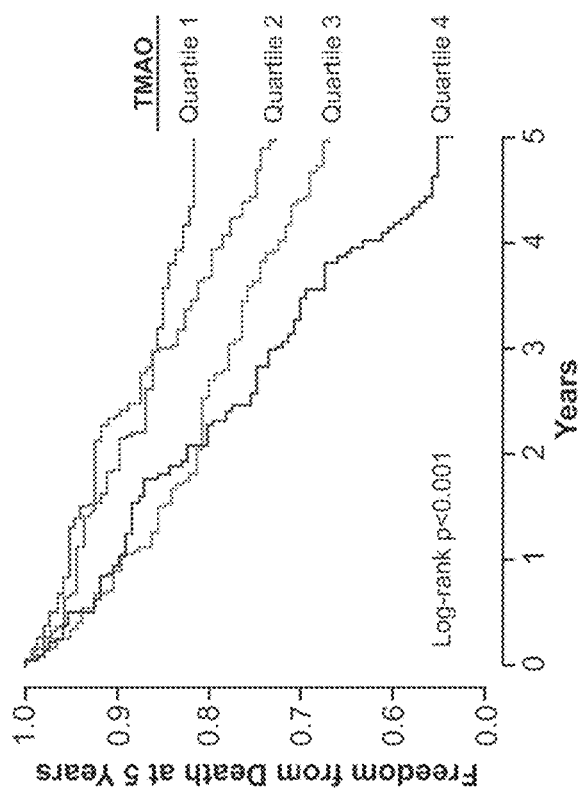
FIGS. 1A-B show the prognostic value of plasma trimethylamine N-oxide (TMAO) levels in Chronic Kidney Disease (CKD). In a cohort of stable cardiac patients undergoing elective diagnostic coronary evaluation, subjects with underlying Stage 3+ chronic kidney disease demonstrated higher levels of fasting plasma TMAO than those with no CKD (p<0.01, FIG. 1A). Increasing quartiles fasting plasma TMAO levels portend increased risk for all-cause mortality at 5 years in patients with CKD (n=521, FIG. 1B).

As used herein, the terms "cardiovascular disease" (CVD) or "cardiovascular disorder" are terms used to classify numerous conditions affecting the heart, heart valves, and vasculature (e.g., veins and arteries) of the body and encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

As used herein, the term "atherosclerotic cardiovascular disease" or "disorder" refers to a subset of cardiovascular disease that include atherosclerosis as a component or precursor to the particular type of cardiovascular disease and includes, without limitation, CAD, PAD, cerebrovascular disease. Atherosclerosis is a chronic inflammatory response that occurs in the walls of arterial blood vessels. It involves the formation of atheromatous plaques that can lead to narrowing ("stenosis") of the artery, and can eventually lead to partial or complete closure of the arterial opening and/or plaque ruptures. Thus atherosclerotic diseases or disorders include the consequences of atheromatous plaque formation and rupture including, without limitation, stenosis or narrowing of arteries, heart failure, aneurysm formation including aortic aneurysm, aortic dissection, and ischemic events such as myocardial infarction and stroke The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION OF THE INVENTION

Provided herein are compositions, systems, and methods for treating a disease, such as kidney and cardiovascular disease, with an agent that reduces the production of trimethylamine (TMA) or trimethylamine-n-oxide (TMAO) in a subject. In certain embodiments, the agent is: i) 3,3-dimethyl-1-butanol (DMB) or a DMB derivative or related compound (e.g., as shown in Table 3), ii) acetylsalicylic acid or derivative thereof (e.g., with an enteric coating for delivery to the colon and/or cecum); iii) a flavin monooxygenase 3 (FMO3) inhibitor; iv) a gut TMA lyase inhibitor; v) an antibiotic or antimicrobial; vi) a probiotic or prebiotic; vii) an antiplatelet agent; or viii) a TMA and/or TMAO sequestering agent.

I. TMA and TMAO Production

The micobiota of humans has been linked to intestinal health, immune function, bioactivation of nutrients and vitamins, and more recently, complex disease phenotypes such as obesity and insulin resistance. It was recently reported that a pathway in both humans and mice link microbiota metabolism of dietary choline and phosphatidylcholine to cardiovascular disease pathogenesis. Choline, a trimethylamine-containing compound and part of the head group of phosphatidylcholine, is metabolized by gut microbiota to produce an intermediate compound known as trimethylamine (TMA). TMA is rapidly further oxidized in the liver by hepatic flavin monooxygenases to form trimethylamine-n-oxide (TMAO), which is proatherogenic and associated with cardiovascular risks. These findings raise the possibility that other dietary nutrients possessing a trimethylamine structure may also generate TMAO from gut microbiota and promote accelerated atherosclerosis.

II. DMB, Derivatives, and Related Compounds

In some embodiments, provided herein are methods for treatment and/or prevention of kidney and/or cardiovascular disease with compounds that inhibit TMAO productions in the gut, such as 3,3-dimethyl-1-butanol (DMB), N,N-dimethylethanolamine (DMEA), N-methylethanolamine (MEA), ethanolamine (EA), trimethylsilyl ethanol, a compound from Table 3, and P,P,P-trimethyl ethanolphosphine; or other compounds represented by Formula I. Formula I is as follows:

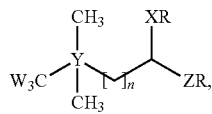

Formula I wherein n is an integer, or n is 0, indicating that CH$_2$ is not present;

wherein Y is C, N, Si, P, S, Ge, Sn, Pb, P, As, Sb, or Bi;

wherein each W is independently selected from: H, Cl, F, Br, or I (e.g., W$_3$C=CH$_3$, CH$_2$Cl, CH$_2$Fl, CH$_2$Br, CH$_2$I, CF$_3$, CCl$_3$, CBr$_3$, Cl$_3$, or CHCl$_2$);

wherein X is O or S and the corresponding bond is either present or absent or double, wherein R is absent, H, an alkyl group, alkenyl group, alkynyl group, phenyl group, amide, alkylamide, or a benzyl group;

wherein Z is C, CH$_2$, CH, NH, O or S, wherein XR is alternatively, H, an ester, thioester, or thionester; glycerol, or one of the following three formulas:

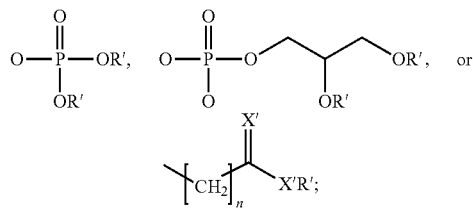

wherein R' is H, an alkyl group, alkenyl group, alkynyl group, phenyl group, or a benzyl group; and wherein X' is O, or S. In certain embodiments, R is amide or alkylamide, and Z is an O, and Z as a double bond O—a carboxylic acid). In some embodiments, the two methyl groups extending from Y are linked by an alkyl or ether to form a 4-6 member ring.

In some embodiments, the present invention provides methods for the treatment and/or prevention of kidney and/or cardiovascular disease comprising: a) identifying a subject as having elevated TMAO and/or TMA levels, and b) administering to the subject a composition comprising N,N-dimethylethanolamine (DMEA), N-methylethanolamine (MEA), ethanolamine (EA), trimethylsilyl ethanol, and P,P,P-trimethyl ethanolphosphine, or a compound represented by Formula I (e.g., dimethylbutanol and/or a derivative thereof), and/or a gut targeting antibiotic and/or a prebiotic (e.g. a fiber containing food that alters intestinal flora composition) and/or a probiotic (e.g., probiotic containing food such as yogurt). In certain embodiments, the composition comprises dimethylbutanol or a compound shown in FIGS. 20-23 of U.S. application Ser. No. 13/915, 299, which is herein incorporated by reference in its entirety. In further embodiments, the identifying comprises viewing results of a TMAO and/or TMA assay (e.g., on paper or on a computer screen) performed on a sample from the subject which show elevated TMAO and/or TMA levels. In certain embodiments, the identifying comprises viewing results of a TMA or TMAO assay performed on a sample or exhaled breath from said subject which show elevated TMA or TMAO levels.

In some embodiments, the composition comprises a compound of Formula I (or N,N-dimethylethanolamine (DMEA), N-methylethanolamine (MEA), ethanolamine (EA), trimethylsilyl ethanol, and P,P,P-trimethyl ethanolphosphine) containing food or beverage. In further embodiments, the composition comprises food or liquid containing a compound of Formula I (or N,N-dimethylethanolamine (DMEA), N-methylethanolamine (MEA), ethanolamine (EA), trimethylsilyl ethanol, and P,P,P-trimethyl ethanolphosphine) selected from the group consisting of but not limited to: olive oil, extra virgin olive oil, grape seed oil, yeast containing food, and red wine. In other embodiments, the composition comprises a compound beneficial for reducing TMAO levels. In certain embodiments, the composition is provided in a pill or capsule (e.g., with a filler or binder). In particular embodiments, the compound of Formula I (e.g., dimethylbutanol) prevent TMA formation from choline or other trimethylamine nutrients (e.g. carnitine, glycerophosphocholine, phosphocholine, phosphatodylcholine) from gut flora, or impairs choline transport. In additional embodiments, the compound of Formula I (or N,N-dimethylethanolamine (DMEA), N-methylethanolamine (MEA), ethanolamine (EA), trimethylsilyl ethanol, and P,P,P-trimethyl ethanolphosphine) induces one or more of the following when administered to a subject: reduced trimethyl amine level, reduce total cholesterol level, reduced LDL level, increased HDL level, and reduced triglyceride level. In further embodiments, the compound of Formula I reduces the risk of kidney and/or cardiovascular disease when administered to a subject.

In some embodiments, Formula I has a formula selected from the group consisting of:

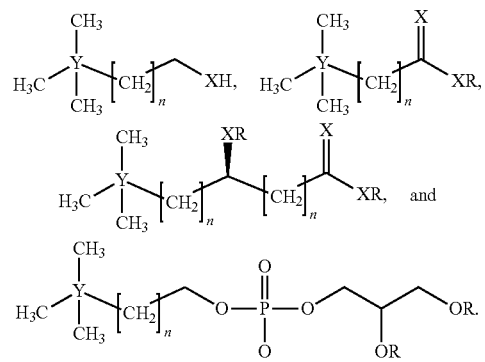

In other embodiments, Formula I has a formula selected from the group consisting of:

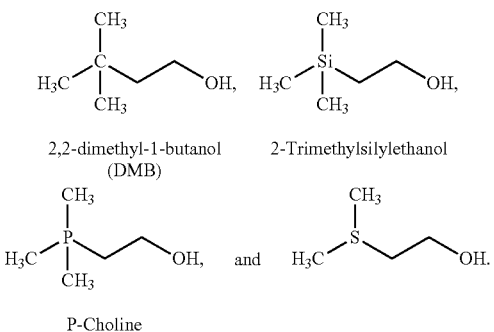

2,2-dimethyl-1-butanol (DMB)   2-Trimethylsilylethanol

P-Choline

In certain embodiments, Formula I has a formula selected from the group consisting of:

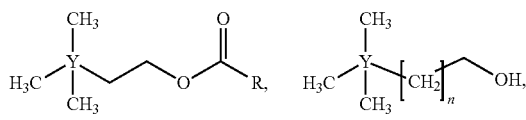

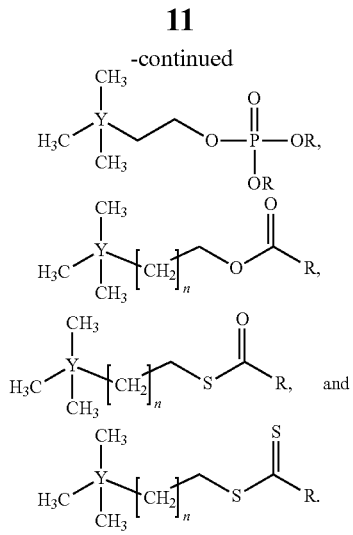

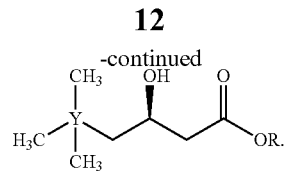

In further embodiments, Formula I has a formula selected from the group consisting of:

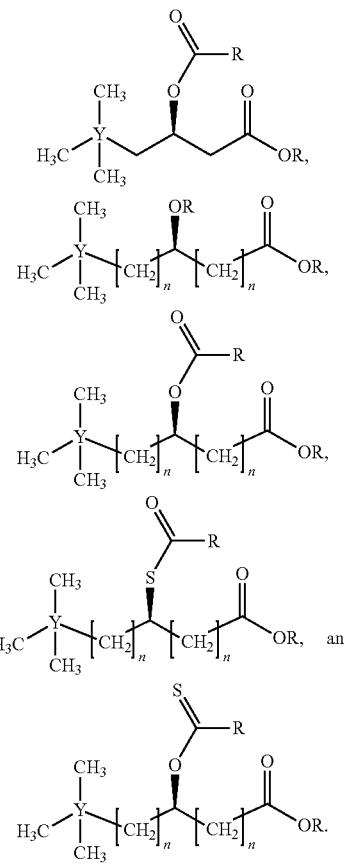

In some embodiments, Formula I has a formula selected from the group consisting of:

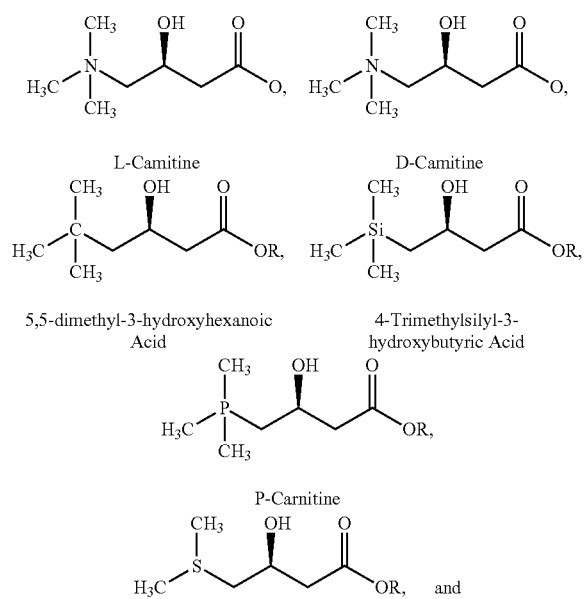

In some embodiments, the compounds of Formula I, or otherwise used in the methods, systems, and compositions here, are those provided in Table 3 below:

TABLE 3

| | |
|---|---|
| Halomethyl cholines:<br>(Fluorocholine, Chlorocholine, Bromocholine, Iodocholine)<br>X = F, Cl, Br, I<br>Y represents counter ions:<br>Y = I, Br, Cl | 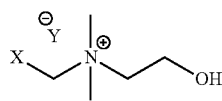 |
| Halomethyl betaines:<br>(Fluorodimethylglycine, Chlorodimethylglycine,<br>Bromodimethylglycine,<br>Iododimethylglycine)<br>X = F, Cl, Br, I | 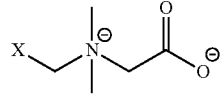 |
| Halomethyl betaine salts:<br>X = F, Cl, Br, I<br>Y represents counter ions:<br>Y = I, Br, Cl | 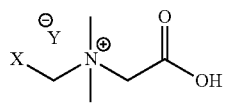 |

TABLE 3-continued

Halomethyl betaine amides:
X = F, Cl, Br, I
Y represents counter ions:
Y = I, Br, Cl

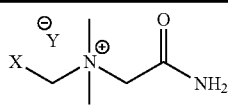

Halomethyl betaine amides:
X = F, Cl, Br, I
Y = I, Br, Cl
R = methyl, ethyl, propyl, amino acids, peptides

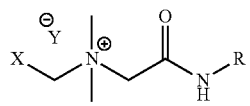

Halomethyl dimethyl amino alcohols:
X = F, Cl, Br, I
Y = I, Br, Cl
R = methyl, ethyl, propyl
(e.g. N-Iodomethyl N,N-dimethylamine-2-hydroxy-propanol,
when X = I, R = methyl)

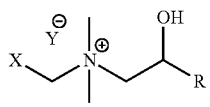

Morpholines:
X = H, F, Cl, Br, I
Y = Cl, Br, I
(e.g. N-methyl-N-(2-hydroxyethyl)morpholine, when X = H)

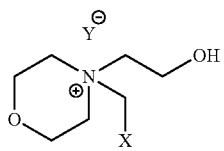

Morpholines:
X = H, F, Cl, Br, I
Y = Cl, Br, I

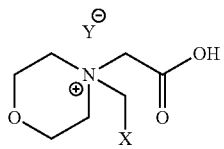

III. Methods for Screening Candidate TMAO and TMA Level Lowering Agents

In some embodiments, the present invention provides drug screening assays (e.g., to screen for TMAO and/or TMA formation inhibitor drugs). In certain embodiments, the screening methods of the present invention utilize trimethylamine containing precursors (e.g., choline, crotonobetaine (cis and trans), gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine) incubated with intestinal microflora, or a cell-free complex of yeaW/yeaX, capable of cleaving TMA-containing compounds to form TMA. For example, in some embodiments, the present invention provides methods of screening for compounds that inhibit the ability of the microflora from cleaving TMA containing precursors to form TMA or using TMA to form TMAO. In some embodiments, candidate compounds are antibiotic compounds, DMB related compound, antimicrobials, candidate TMA lyase inhibitors, or candidate FMO3 inhibitors (e.g., from a small molecule library).

In one screening method, candidate compounds are evaluated for their ability to inhibit TMA formation by microflora or a cell-free complex of yeaW/yeaX by contacting a candidate compound with a sample containing the microflora or a cell-free complex of yeaW/yeaX and TMA containing precursors and then assaying for the effect of the candidate compounds on TMA formation. In some embodiments, the effect of candidate compounds on TMA formation is assayed for by detecting the level of TMA formed.

The test compounds of the present invention can be obtained, for example, using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are generally preferred for use with peptide libraries, while the other four approaches are applicable to peptide, non-peptide oligomer or small molecule libraries of compounds (Lam (1997) Anticancer Drug Des. 12:145).

In certain embodiments, the test compounds are antibiotics. Any type of antibiotic may be screened (or used to treat disease, such as kidney disease). Examples of such antibiotics include, but are not limited to, Ampicillin; Bacampicillin; Carbenicillin Indanyl; Mezlocillin; Piperacillin; Ticarcillin; Amoxicillin-Clavulanic Acid; Ampicillin-Sulbactam; Benzylpenicillin; Cloxacillin; Dicloxacillin; Methicillin; Oxacillin; Penicillin G; Penicillin V; Piperacillin Tazobactam; Ticarcillin Clavulanic Acid; Nafcillin; Cephalosporin I Generation; Cefadroxil; Cefazolin; Cephalexin; Cephalothin; Cephapirin; Cephradine; Cefaclor; Cefamandol; Cefonicid; Cefotetan; Cefoxitin; Cefprozil; Ceftmetazole; Cefuroxime; Loracarbef; Cefdinir; Ceftibuten; Cefoperazone; Cefixime; Cefotaxime; Cefpodoxime proxetil; Ceftazidime; Ceftizoxime; Ceftriaxone; Cefepime; Azithromycin; Clarithromycin; Clindamycin; Dirithromycin; Erythromycin; Lincomycin; Troleandomycin; Cinoxacin; Ciprofloxacin; Enoxacin; Gatifloxacin; Grepafloxacin; Levofloxacin; Lomefloxacin; Moxifloxacin; Nalidixic acid; Norfloxacin; Ofloxacin; Sparfloxacin; Trovafloxacin; Oxolinic acid; Gemifloxacin; Perfloxacin; Imipenem-Cilastatin Meropenem; Aztreonam; Amikacin; Gentamicin; Kanamycin; Neomycin; Netilmicin; Streptomycin; Tobramycin;

Paromomycin; Teicoplanin; Vancomycin; Demeclocycline; Doxycycline; Methacycline; Minocycline; Oxytetracycline; Tetracycline; Chlortetracycline; Mafenide; Silver Sulfadiazine; Sulfacetamide; Sulfadiazine; Sulfamethoxazole; Sulfasalazine; Sulfisoxazole; Trimethoprim-Sulfamethoxazole; Sulfamethizole; Rifabutin; Rifampin; Rifapentine; Linezolid; Streptogramins; Quinopristin Dalfopristin; Bacitracin; Chloramphenicol; Fosfomycin; Isoniazid; Methenamine; Metronidazol; Mupirocin; Nitrofurantoin; Nitrofurazone; Novobiocin; Polymyxin; Spectinomycin; Trimethoprim; Colistin; Cycloserine; Capreomycin; Ethionamide; Pyrazinamide; Para-aminosalicyclic acid; and Erythromycin ethylsuccinate.

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994). Libraries of compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249:404-406 (1990); Cwirla et al., Proc. Natl. Acad. Sci. 87:6378-6382 (1990); Felici, J. Mol. Biol. 222:301 (1991)).

The ability of the test compound to inhibit TMA formation by intestinal microflora, or a cell-free complex of yeaW/yeaX, can be monitored by detectably labeling the TMA portion of a TMA containing precursor compound. Such detectable labels include, for example, radioisotopes, chromophores, fluorophores, or enzymatic labels. For example, TMA containing precursors can be labeled with $^{125}I$, $^{35}S$ $^{14}C$ or $^3H$, either directly or indirectly, and the radioisotope detected by direct counting of radioemission or by scintillation counting. Alternatively, TMA containing precursor can be enzymatically labeled with, for example, horseradish peroxidase, alkaline phosphatase, or luciferase, and the enzymatic label detected by determination of conversion of an appropriate substrate to product. In one embodiment, the TMA containing precursor or the test substance is anchored onto a solid phase. The TMA containing precursor anchored on the solid phase can be detected at the end of the reaction.

In certain embodiments, cell free assays can be conducted in a liquid phase using a complex of yeaW/yeaX. In such an assay, the reaction products are separated from unreacted components, by any of a number of standard techniques, including, but not limited to: differential centrifugation (see, for example, Rivas and Minton, Trends Biochem Sci 18:284-7 (1993)); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 (1998); Hageand Tweed J. Chromatogr. Biomed. Sci. Appl 699:499-525 (1997)).

This invention further pertains to agents identified by the above-described screening assays. Accordingly, it is within the scope of this invention to further use an agent identified as described herein in an appropriate animal model to determine the efficacy, toxicity, side effects, or mechanism of action, of treatment with such an agent. Furthermore, novel agents identified by the above-described screening assays can be used for treatments as described herein.

EXAMPLES

The following examples are for purposes of illustration only and are not intended to limit the scope of the claims.

Example 1

The Gut Microbiota-Dependent TMAO Pathway Contributes to Development of Renal Insufficiency and Mortality Risk in Chronic Kidney Disease This example describes an examination of the contribution of TMAO to the development of renal insufficiency and mortality risk in chronic kidney disease (CKD).

Methods

Human Studies. The human population studied is a single-center, prospective cohort approved by the Cleveland Clinic Institutional Review Board. Adult subjects (ages 18 years and above) were included who underwent elective diagnostic coronary angiography for cardiac evaluation from 2001-2007 as previously described (9). Subjects with known acute coronary syndromes or revascularization procedures within 30 days of enrollment, or history of congenital heart disease, were excluded. After informed consent, fasting plasma blood samples were collected using ethylenediaminetetraacetic acid tubes prior to any drug administration via the arterial sheath, and immediately processed and frozen in $-80°$ C. until analysis. Estimated glomerular filtration rate (eGFR) was calculated according to the CKD-EPI creatinine and cystatin C formula (17), with CKD defined as eGFR >60 ml/min/1.73 m2 (CKD stage 3 or beyond). Ascertainment of all-cause mortality at 5-years was performed by prospective telephone contact and chart review plus interrogation of the Social Security Death Index (up to 2011).

Plasma Analysis. Trimethylamine-N-oxide (TMAO) levels were determined by stable isotope dilution high-performance liquid chromatography with online electrospray ionization tandem mass spectrometry (LC/MS/MS) on an AB SCIEX 5500 triple quadrupole mass spectrometer (AB SCIEX, Framingham Mass.) using d9-(trimethyl)-labeled internal standards as previously described (10, 18). High-sensitivity C-reactive protein (hsCRP), fasting lipid panel, cystatin C, and serum creatinine were measured using the Architect ci8200 platform (Abbott Laboratories, Abbott Park, Ill.).

Animal Study. To directly test for a potential contribution of dietary choline or TMAO to promotion of renal dysfunction, C57BL6J mice were fed with the following diets for 6 weeks: i) a chemically defined diet comparable in composition to standard chow diet (Teklad 2018, Harland Laboratories) that contains 0.08% (gm/gm) total choline; ii) the same diet supplemented with choline (1% total); and iii) the same diet supplemented with TMAO (0.12%). A separate study included C57BL6J mice with ApoE−/− background were fed with the same diet groups for comparing their cystatin C levels at 14 weeks of follow-up using a commercially available mouse enzyme-linked immunosorbent assay (R&D systems, Minneapolis Minn.). This study has been approved by the Cleveland Clinic Institutional Animal Care and Use Committee.

Quantitative Histologic Techniques. Mason's trichome staining was performed on deparafinized 5 μm serial kidney sections. The kidney sections were mounted under a Leica DM 2500 microscope and digitized with a QImaging Micro-Publisher 5.0 RTV camera for wide field microscopy. Quantitative morphometric analysis was performed on cortical fields (at least 8 from each animal) lacking major blood vessels and the collagen volume was determined using automated (for batch analysis) and customized algorithms/scripts (ImageIQ Inc., Cleveland, Ohio) written for Image Pro Plus 7.0. Briefly, a set of representative images are chosen that demonstrated a wide range of staining intensities and prevalence. In an automated script, these "training" images were loaded one after another prompting the user to delineate "blue" pixels representing positive collagen staining using an interactive color picking tool. An iterative color profile or classifier was generated and subsequently applied to all images in a given directory using a fully automated algorithm. Positive pixels, as defined by the color profile, were segmented and summed to provide positive staining area. Total tissue area was determined by extracting the "saturation" channel, applying a lo-pass filter, and thresholding the result. Any area within the general tissue boundary that was empty (i.e. white) was removed by converting the original image to grayscale and applying a fixed threshold for non background pixels on adequately white-balanced images. Finally, total tissue area and total stained area were exported to Excel. For post-processing verification, segmented regions were superimposed onto the original image (green outlines) and saved for each image analyzed.

Preparation of Tissue Homogenates and Immunoblotting. Equal amounts of protein were prepared using standard biochemical methods and subjected to SDS-PAGE and electrotransfer of proteins from gels to Immobilon-P membranes (Millipore). Membranes were incubated with the following antibodies: SMAD3 and phospho-SMAD-3(Ser423/425) (Cell Signaling Technology); tubulin (Santa Cruz Biotechnology); KIM-1 (Novus Biologicals). Detection for all immunoblots was performed with the SNAP i.d.™ Protein Detection System (Millipore) and Super Signal Chemiluminescent Substrate Products (Pierce), and band intensity was analyzed by densitometry (ImageQuant™, GE Healthcare).

Statistical Analyses. Continuous variables were summarized as mean±standard deviation if normally distributed and median (interquartile ranges [IQR]) if non-normally distributed. The student's t-test or Wilcoxon-Rank sum test for continuous variables and chi-square test for categorical variables were used to examine the difference between groups. Spearman's correlation was used to examine the associations between TMAO and other laboratory measurements. Kaplan-Meier survival plots and Cox proportional hazards analysis were used to determine Hazard ratio (HR) and 95% confidence intervals (95% CI) for all-cause mortality stratified according to TMAO in quartiles. Adjustments were made for individual traditional risk factors including age, sex, systolic blood pressure, low-density lipoprotein cholesterol (LDLc), high-density lipoprotein cholesterol (HDLc), smoking, diabetes mellitus, log-transformed hsCRP, and logtransformed eGFR to predict all-cause mortality risks. Net reclassification and area under Receiver Operator Characteristic curve were calculated according to mortality risk estimated using Cox models adjusted for above mentioned traditional risk factors with versus without TMAO as previously described 19. All analyses performed used R 2.15.1 (Vienna, Austria). P<0.05 was considered statistically significant.

Results

Elevated TMAO in Patients with Renal Insufficiency Portend Poorer Survival. Baseline clinical and laboratory characteristics of the cohort are reported in Table 1.

TABLE 1

Baseline Characteristics

| Characteristic | eGFR ≥ 60 (n = 3,166) | eGFR < 60 (n = 521) | p-value |
|---|---|---|---|
| Age (years) | 62 ± 11 | 70 ± 10 | <0.001 |
| Male (%) | 66 | 48 | <0.001 |
| Diabetes (%) | 27 | 53 | <0.001 |
| Hypertension (%) | 69 | 88 | <0.001 |
| Smoking (%) | 66 | 61 | 0.047 |
| History of MI (%) | 40 | 53 | <0.001 |
| History of stroke (%) | 5 | 13 | <0.001 |
| History of CABG (%) | 28 | 42 | <0.001 |
| History of PCI (%) | 31 | 30 | 0.728 |
| LDL (mg/dL) | 97 (79-118) | 93 (72-114) | <0.001 |
| HDL (mg/dL) | 34 (28-41) | 32 (26-40) | <0.001 |
| hsCRP (mg/L) | 2.2 (0.9-5.0) | 4.1 (1.8-9.6) | <0.001 |
| eGFR (ml/min/1.73 m$^2$) | 89 (78-101) | 49 (38-55) | <0.001 |
| Cystatin C (mg/L) | 0.9 (0.8-1) | 1.5 (1.3-1.8) | <0.001 |
| ACE inhibitor/ARB (%) | 48 | 66 | <0.001 |
| Statins (%) | 61 | 59 | 0.437 |
| Beta blockers (%) | 63 | 68 | 0.04 |
| Aspirin (%) | 75 | 67 | <0.001 |
| TMAO (μM) | 3.4 (2.3-5.3) | 7.9 (5.2-12.4) | <0.001 |

Figure 1A:
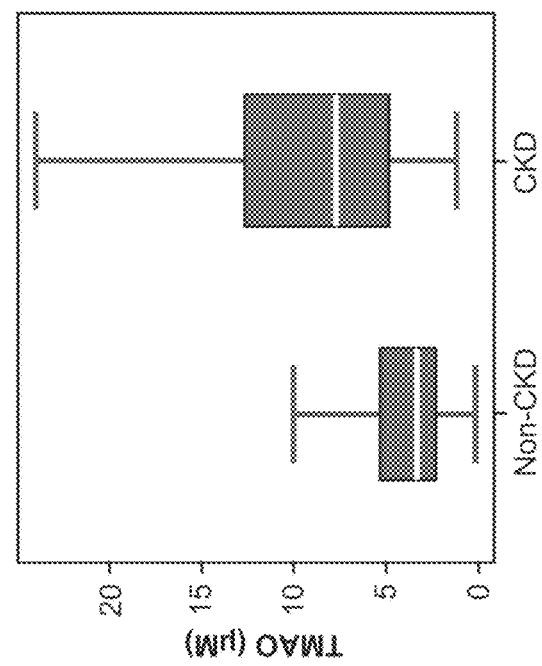

A total of 3,687 subjects were included in this analysis, among which 521 subjects fulfilled criteria for CKD and 3,166 subjects for non-CKD. Compared to non-CKD subjects, TMAO levels were elevated in patients with CKD (median TMAO: 7.9 [IQR 5.2-12.4]uM versus 3.4 [IQR 2.3-5.3]uM, p<0.001; FIG. 1A). Overall in the CKD cohort, TMAO modestly correlated with eGFR (r=−0.48, p<0.001) and cystatin C (r=0.46, p<0.001), but only weakly correlated with hsCRP (r=0.04, p=0.332).

In the CKD cohort, higher TMAO levels (quartiles 4 versus 1) were associated with a 2.8-fold increase in risk for all-cause mortality at 5 years (unadjusted HR 2.76, 95% CI 1.74-4.37, p<0.001). After adjusting for traditional CVD risk factors, log-transformed hsCRP, and log-transformed eGFR, higher TMAO levels still were associated with a 1.9-fold poorer 5-year survival (adjusted HR 1.93, 95% CI 1.13-3.29, p<0.05; Table 2, Kaplan-Meier curve shown in FIG. 1B).

TABLE 2

Cox Proportional Hazards Analysis of Plasma TMAO Levels Stratified at quartile Levels in Predicting Risk of All-cause Mortality at 5 Years Stratified by CKD and Non-CKD Cohorts

| | TMAO (range) | | | |
|---|---|---|---|---|
| | Quartile 1 | Quartile 2 | Quartile 3 | Quartile 4 |
| | CKD Cohort (n = 521) | | | |
| Range (μM) | <5.2 | 5.2-7.9 | 7.9-12.4 | ≥12.4 |
| Events | 26/129 (20.2%) | 42/131 (32.1%) | 43/130 (33.1%) | 63/131 (48.1%) |
| Unadjusted HR | 1 | 1.70 (1.04-2.79)* | 1.75 (1.07-2.87)* | 2.76 (1.74-4.37)** |
| Adjusted HR | 1 | 1.42 (0.85-2.35) | 1.51 (0.90-2.51) | 1.93 (1.13-3.29)* |

TABLE 2-continued

Cox Proportional Hazards Analysis of Plasma TMAO Levels Stratified at quartile Levels in Predicting Risk of All-cause Mortality at 5 Years Stratified by CKD and Non-CKD Cohorts

| | TMAO (range) | | | |
|---|---|---|---|---|
| | Quartile 1 | Quartile 2 | Quartile 3 | Quartile 4 |
| | Non-CKD Cohort (n = 3166) | | | |
| Range (mM) | <2.3 | 2.3-3.4 | 3.4-5.3 | ≥5.3 |
| Events | 48/787 (5.1%) | 59/793 (7.4%) | 81/791 (10.2%) | 104/795 (13.1%) |
| Unadjusted HR | 1 | 1.22 (0.83-1.79) | (1.19-2.43)** | 2.21 (1.57-3.12)** |
| Adjusted HR | 1 | 1.08 (0.74-1.58) | 1.23 (0.84-1.78) | 1.47 (1.02-2.12)* |

When stratified according to median levels (7.9 uM), higher TMAO conferred a 1.7-fold increase in risk for all-cause mortality (HR 1.70, 95% CI 1.25-2.30, p<0.001), and remained significant after adjusting for traditional risk factors and log-transformed hsCRP (adjusted HR 1.72, 95% CI 1.16-2.34, p<0.001), as well as with addition of cystatin C to the model (adjusted HR 1.45, 95% CI 1.05-2.02, p<0.05). Using median cohort cut-offs with low cystatin C (<1.4 mg/dL) and low TMAO (<7.9 uM) as reference, those with concomitant high cystatin C and high TMAO had a 3-fold increase in mortality risk (HR 3.01, 95% CI 1.97-4.59, p<0.001). These findings are consistent with the notion that elevated TMAO is associated with poor prognosis in patients with established CKD.

Figure 2:
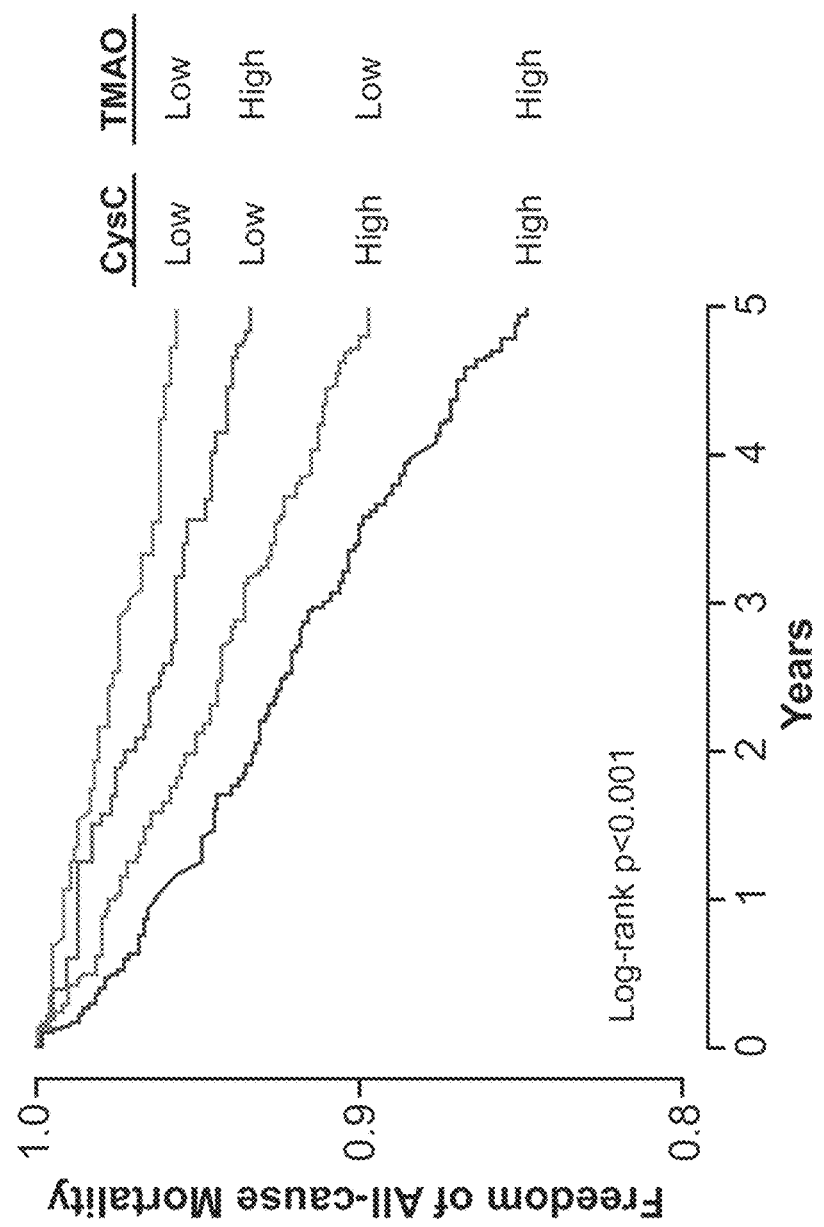
FIG. 2 shows comparative prognostic value of plasma TMAO and Cystatin C in patients with no Chronic Kidney Disease. Subjects with elevated cystatin C (>0.9 mg/dL) and TMAO (>3.4 uM) had the highest 5-year mortality risk in this non-CKD cohort (n=3,188).

Increased TMAO Levels in Non-CKD Patients with Elevated Cystatin C. Within the non-CKD cohort (n=3,166), the prognostic value of elevated TMAO (quartile 4 vs 1) remained predictive of 5-year mortality risk (HR 2.21, 95% CI 1.57-3.12, p<0.001), as well as after adjusting for traditional risk factors, log-transformed hsCRP, and logtransformed eGFR (adjusted HR 1.47, 95% CI 1.02-2.12, p<0.05, Table 2B). These findings were similar when restricted to subjects with preserved eGFR (≥60 ml/min/1.73 m2) plus normal cystatin C (<1.4 mg/dL, n=3,151). Elevated TMAO levels is associated with higher 5-year mortality risk in both normal and elevated cystatin C levels (FIG. 2). Using median cohort cut-offs with low cystatin C (<0.9 mg/dL) and low TMAO (<3.4 uM) as reference, those with concomitant high cystatin C and high TMAO had a 3.7-fold increase in mortality risk (HR 3.67, 95% CI 2.57-5.23, p<0.001).

Dietary Choline and TMAO Promotes Renal Fibrosis and Dysfunction in Animal Models.

Figure 3A:
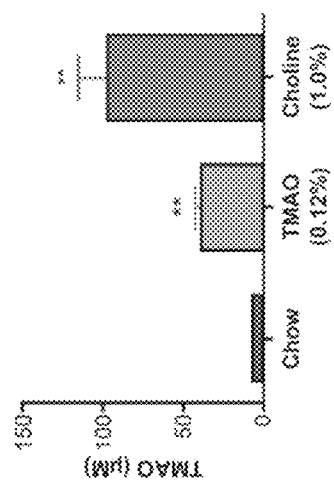
FIGS. 3A-F show dietary choline/TMAO exposure contributes to progressive renal fibrosis. Plasma TMAO (A) levels are increased after 6 week feeding TMAO (0.12%), or Choline (1.0%) diets vs chow (0.08% choline) fed mice. Representative Mason trichrome histology (B) quantitative morphometry (C) and its relationship with TMAO levels (D), SMAD3 activation by phosphorylation at serine 423/425 (E) and its relationship with TMAO levels (F) in mouse kidneys after 6 week feeding of chow (0.08% choline), TMAO (0.12%), and Choline (1.0%) diets. Scale bar represents 100 um. **P<0.01 vs. chow fed, n≥5 mice per group.
Figure 3B:
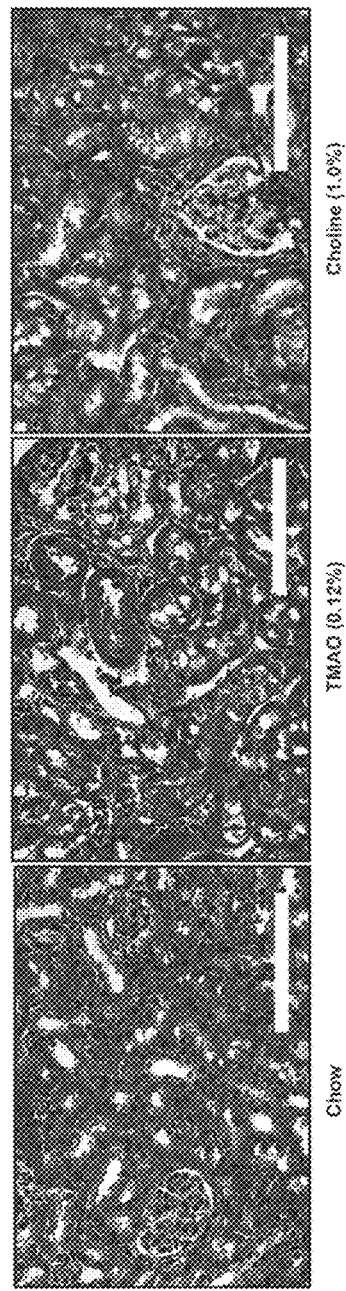
Figure 3C:
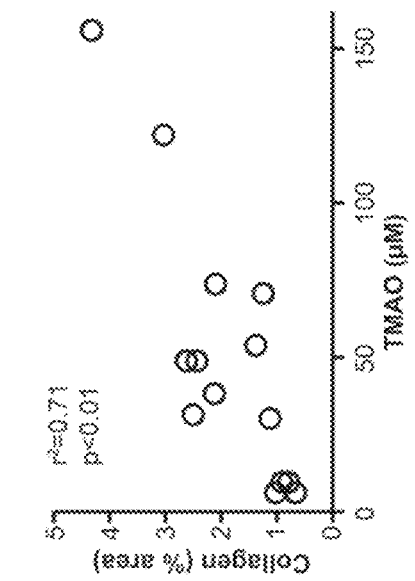
Figure 3D:
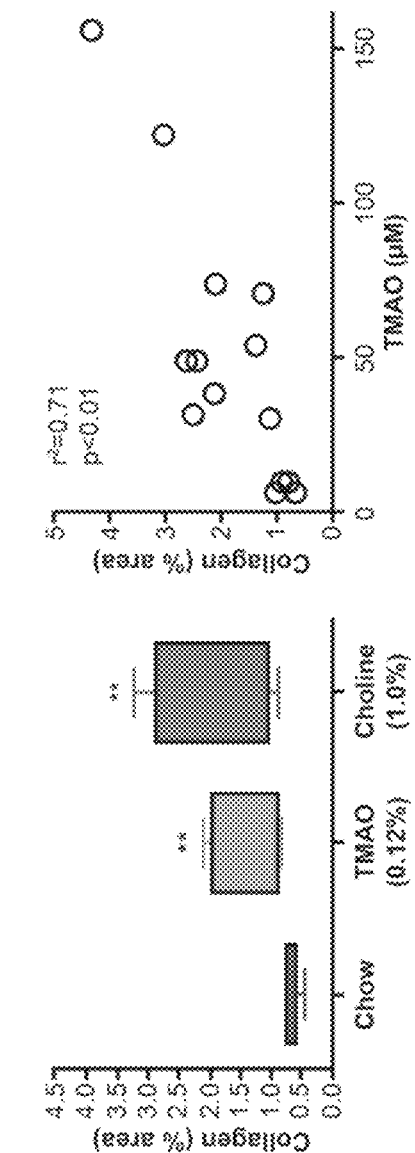
Figure 3E:
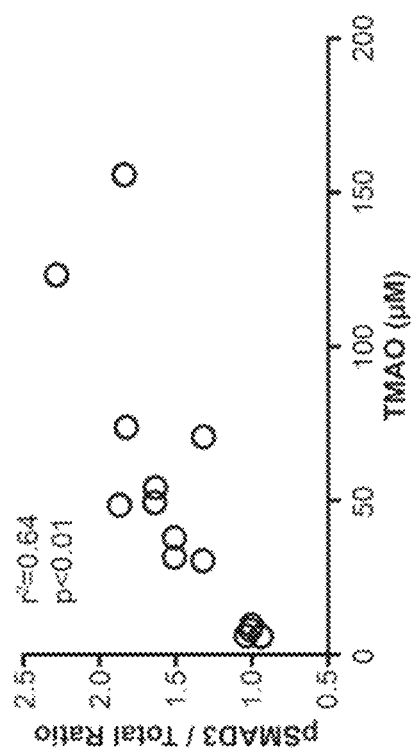
Figure 3F:
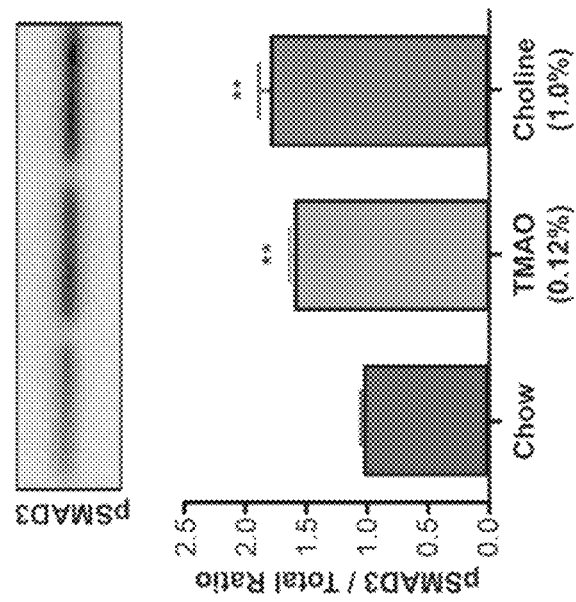
Figure 4A:
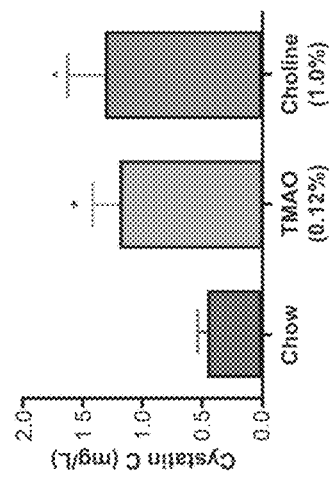
FIGS. 4A-C show that dietary choline/TMAO exposure contributes to progressive renal injury and dysfunction. Immunoblot of KIM-1 expression (A) and its relationship with TMAO levels (B) in mouse kidneys after 6 week feeding of chow (0.08% choline), TMAO (0.12%), and choline (1.0%) diets. Also shown are plasma cystatin C levels (C) after 16 week feeding of chow, TMAO (0.12%), and Choline (1.0%) diets. **P<0.01 vs. chow fed, n≥5 mice per group.
Figure 4B:
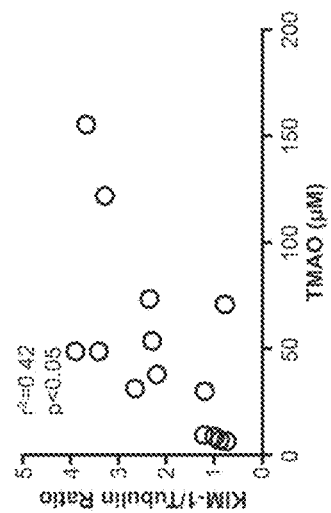
Figure 4C:
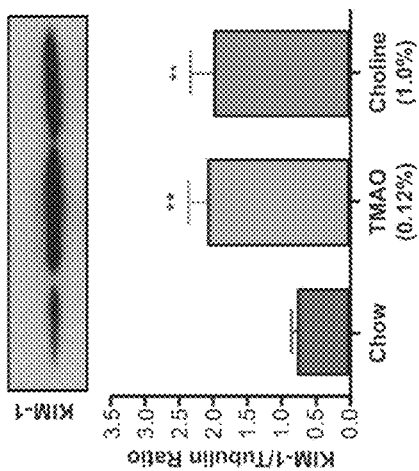

To directly test the hypotheses that either dietary TMAO itself, or dietary nutrients that contribute to gut microbiota dependent production of TMAO, can impact development and progression of CKD, animal model studies were performed. Conventionally housed 8-week old male mice (C57BL/6J background) were fed ad libitum a chemically defined diet comparable to normal chow (0.08 gm % choline), or the same diet supplemented with either choline (1.0% final) or TMAO (0.12%), as described under Methods. After 6 weeks, significant (p<0.01) increases were observed in TMAO levels in both the TMAO supplemented and choline-supplemented groups of mice (FIG. 3A), with TMAO levels observed within the range of values detected among CKD subjects studied (97.5 percentile 77.6 uM, 99 percentile 96.3 uM). Importantly, elevated TMAO levels were associated with corresponding increases in parenchymal fibrosis and collagen deposition (FIGS. 3B-C) and phosphorylation of Smad3, an important regulator of the pro-fibrotic TGF-β/Smad3 signaling pathway during fibrotic kidney disease 20 (FIG. 3E). Furthermore, TMAO-fed and choline-fed mice experienced increased kidney injury marker-1 (KIM-1, FIG. 4A). Extending the TMAO/choline feeding to 16 weeks was associated with increased serum cystatin C levels compared to chow-fed mice (FIG. 4C). Upon further examination, striking dose-dependent relationships were noted between plasma TMAO levels and monitored indices of renal histopathological (FIG. 3D, 3F) and functional impairment (FIG. 4B).

Discussion

There are several key findings in this Example. First, in subjects with CKD, it was observed that TMAO levels are not only elevated compared to non-CKD subjects, but importantly, portend poorer overall survival. Second, it was observed that within the non-CKD cohort, higher levels of TMAO portend poorer survival both within the cohort of low levels as well as high levels of cystatin C (stratified at median levels). Interestingly, the prognostic value for the highest TMAO quartile in predicting future mortality risk in this cohort remained robust even after adjustment for traditional risk factors. Third, extending to animal models studies, dietary exposure of either choline or TMAO lead to the development of renal parenchymal fibrosis and early measures of dysfunction (elevated cystatin C). These studies thus suggest both a causal relationship and clinical relevance of dietary choline-induced, gut microbiota-mediated TMAO formation in CKD development and progression.

Trimethylamine N-oxide is a low molecular weight compound that is easily filtered by the kidney, and effectively removed by hemodialysis (13). Considered a nitrogenous waste product whose levels rise with diminished renal function, elevated TMAO levels have been reported in small cohorts (n<20) of subjects with either end-stage renal disease, or CKD, where levels were shown to correlate with both serum urea and creatinine (15). Detailed animal and human experiments on the renal clearance of methylamines such as TMA and TMAO have been performed, confirming the kidneys as the primary elimination route (21). Interestingly, the urinary clearances of both TMA and TMAO are higher than the glomerular filtration rate, and TMAO clearance also decreases with increasing dose, which suggests that saturable renal tubular secretion occurs (22). The majority of a dose of TMA is also excreted in the urine, with varying proportions in the forms of TMA and TMAO being dependent on the dose level (23). Urinary TMAO levels are reported to rise with episodes of kidney graft dysfunction in renal transplant recipients, suggesting an intrinsic accumulation of TMAO (presumably as an osmolyte like urea) that is released during damage of the renal medullary cells (24-27). The mechanistic link between elevated TMAO and adverse prognosis in CKD and even in the setting of subclinical renal insufficiency (elevated cystatin C) in non-CKD patients observed in this Example is therefore consistent with the heightened risk of developing CKD in the CKD population.

These results from animal studies showed for the first time a direct mechanistic link between dietary choline, or dietary TMAO, and progressive renal fibrosis and dysfunction. Indeed, both brief exposure (6 weeks) to either a high choline diet or a diet supplemented directly with TMAO both led to increased levels of the early kidney injury marker KIM-1, and enhanced phosphorylation of Smad3, an important regulator of renal fibrosis (28). A more prolonged exposure to either the high choline diet or the TMAO supplemented diet both led to increased plasma levels of cystatin C, a sensitive indicator of renal functional impairment. Interestingly, a recent untargeted metabolomic study from the Framingham Heart Study identified elevated choline and TMAO levels were associated with an increased future risk of developing CKD (29). The animal model findings of this Example therefore provide a potential mechanistic rationale for the Framingham observational data, and collectively, further link elevated TMAO levels with increased susceptibility of CKD.

The prospects that exposure to specific dietary nutrients via gut microbiota may impact susceptibility to the development and progression of both CKD and CVD has important potential public health implications. Randomized nutritional intervention studies in CKD patients to date have not explored a potential role for choline, phosphatidylcholine, L-carnitine or TMAO (which can be abundant in certain types of fish) in disease progression. Similarly, epidemiological studies are rather limited on the topic of diet and CKD risks, even though a recommended renal diet is typically low in protein intake.

Dietary management of CKD patients represents a challenge, and much less is known about nutritional factors that might predispose to enhanced risk for development of CKD or its progression. Interestingly, in a sub-study (n=3,296) amongst women who had urine microalbumin levels available from the Nurses Health Study, two or more servings of red meat (primary source of L-carnitine) per week were directly associated with enhanced risk for development of microalbuminuria (OR: 1.51; 95% CI: 1.01 to 2.26) (30. Based upon the present Example, a diet monitored by following TMAO levels and designed to limit TMAO precursors (low in red meat, meats, liver, egg yolk, and high fat dairy products) and TMAO itself (certain fish) would be an attractive diet to limit the rate of CKD progression.

Collectively, the present data indicate a dietary-induced, intestinal microbiota-dependent mechanism contributes to both progressive renal fibrosis and dysfunction, and mortality risks, among subjects with CKD. They also build upon the recent body of evidence demonstrating a mechanistic link between gut microbiota-associated metabolic dysregulation and cardiovascular risk in humans (8-11). The discovery of the metaorganismal pathway involved in TMAO generation thus affords a unique opportunity to systematically investigate the potential contributions of discrete participants in the overall diet→microbe→host enzyme pathways for TMAO formation and development and progression of cardio-renal dysfunction, thereby offering insights into modulation of such pathways. It is interesting that in both animal models and patients with established CKD, pre- and probiotic intervention studies have been performed, with reports of changes in gut microbiota composition and activity. For example, *lactobacillus acidophilus* or *bifidobacterium* have been reported to reduce inflammatory signaling associated with the microbiota-derived metabolites that accumulate in CKD (31-34), in addition to modestly improving renal function (35, 36). Similarly, prebiotic compound use to interrupt pathways that lead to gut microbiota derived uremic toxins such as indoxyl sulfate and p-cresyl sulfate has shown some efficacy in both human and animal trials of CKD (5, 37).

Example 2

ACE (Acetylsalicylic Acid) Reduction of TMAO Production In Vivo

This Example investigated the question of whether aspirin can aspirin (ASA) mitigate the prothrombotic phenotype associated with high choline or TMAO related diet. And if so, is there evidence that aspirin therapy itself impacts TMAO production in vivo, and could this be a mechanism through which aspirin promotes some of its cardiovascular benefit.

In the first part of this Example, the impact of aspirin (ASA) therapy on the prothrombotic phenotype provoked by chronic choline supplementation in the diet was examined. This diet elevates TMAO, and provokes enhanced platelet responsiveness and thrombosis. C57BL/6J females mice were placed on a chemically defined diet comparable to the normal mouse feed (chow) vs. an identical diet supplemented with 0.5 gm % choline (choline). Each of these two groups of mice were then split, and half placed on aspirin therapy at a dose comparable to that used in humans (ASA 4 mg/Kg BW in drinking water). After 2 weeks, plasma was collected for TMAO levels by established stable isotope dilution LC/MS/MS analyses. In parallel, in vivo thrombosis potential was measured using the well established carotid artery FeCl exposure model with vital microscopy. In this model, the internal carotid artery is exposed by cutdown, and visualized by computer imaging software using vital microscopy. Platelets are removed and fluorescently labeled, and then infused in the contralateral jugular vein. Following FeCl exposure, one can monitor clot formation directly over time by visualizing the carotid artery at the site of FeCl application. One can also monitor blood flow down stream from the clot formation. Thus, one can both quantify clot formation, and time to blood flow cessation downstream from the clot. Either of these represent quantitative indices of thrombosis potential in vivo.

Figure 5:
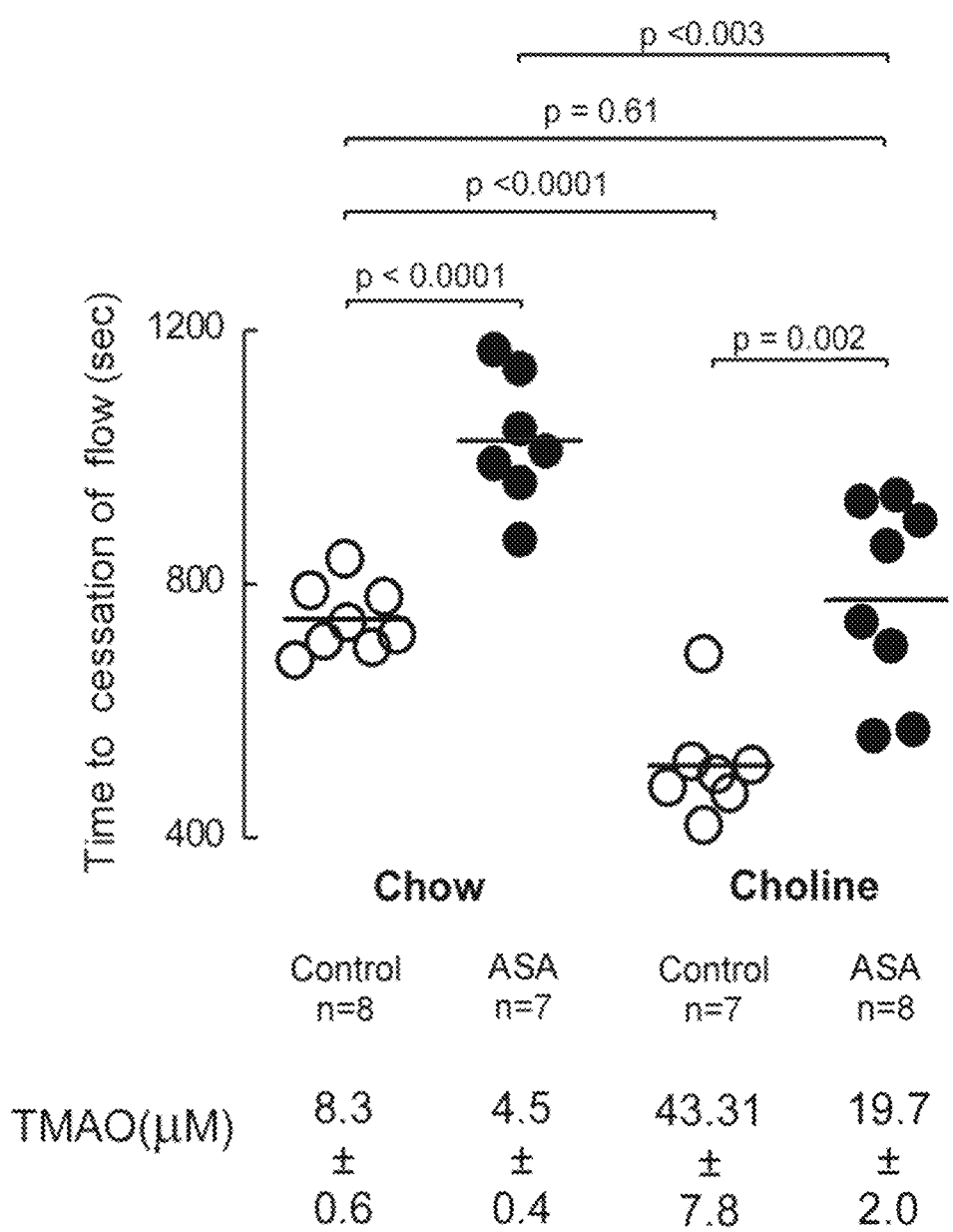
FIG. 5 show results from Example 2 and specifically shows that a choline diet fosters a prothrombotic phenotype and that aspirin use attenuates TMAO levels.

FIG. 5 shows the results of this work. Along the bottom in FIG. 5, the levels of TMAO monitored in plasma are displayed. Note first that choline diet induced a significant increase in TMAO (8.3 vs 43.31 uM; p<0.05 for chow vs choline without aspirin(ASA)). A similar increase in TMAO is noted in mice on ASA concurrently with choline diet (4.5 vs 19.7; p<0.05 for chow vs choline groups on ASA). Also note that in both diets (chow and choline) addition of ASA resulted in significant reduction in TMAO level (approx. 2-fold; p<0.05 for comparison in each diet). Thus, these studies show that ASA therapy lowers TMAO levels. In the in vivo thrombosis studies, it is noted that choline diet alone reduces the time to blood flow cessation (prothrombotic; p<0.0001). However, addition of ASA to the choline diet attenuates the extent of prothrombotic phenotype observed. For example, the choline diet+ASA group shows no difference in time to blood flow cessation relative to the control (chow and no ASA) group. Of note, the addition of choline into the diet still impacts time to blood flow cessation and hence promotes a prothrombotic effect still in ASA treated groups, even though the ASA promotes an improvement (comparison of chow+ASA vs choline+ASA reveals significant prothrombotic effect of choline diet still with ASA therapy).

Collectively, this work indicates: 1) in the setting of elevated TMAO, where a prothrombotic effect is generated, addition of aspirin may mitigate the adverse effect. 2) ASA therapy can be used to lower TMAO. This suggests ASA can be used, for example, as a therapy to inhibit microbial TMA lyases, the rate limiting step in TMAO production in vivo. 3) Elevated TMAO levels may serve as an indication for antiplatelet related interventions, such as aspirin, and other antiplatelet drugs (e.g., clopidegrel, prasugrel); abciximab (Reopro®); Aggrenox® (dipyridamole/ASA); anagrelide (Agrylin®); cilostazol (Pletal®); clopidogrel (Plavix®); dipyridamole (Persantine®); eptifabatide (Integrilin®); prasugrel-EFFIENT™; ticagrelor (BRILINTA™); ticlopidine (Ticlid®); tirofiban (Aggrastat®); and vorapaxar (ZONTIVITY™).

Figure 6:
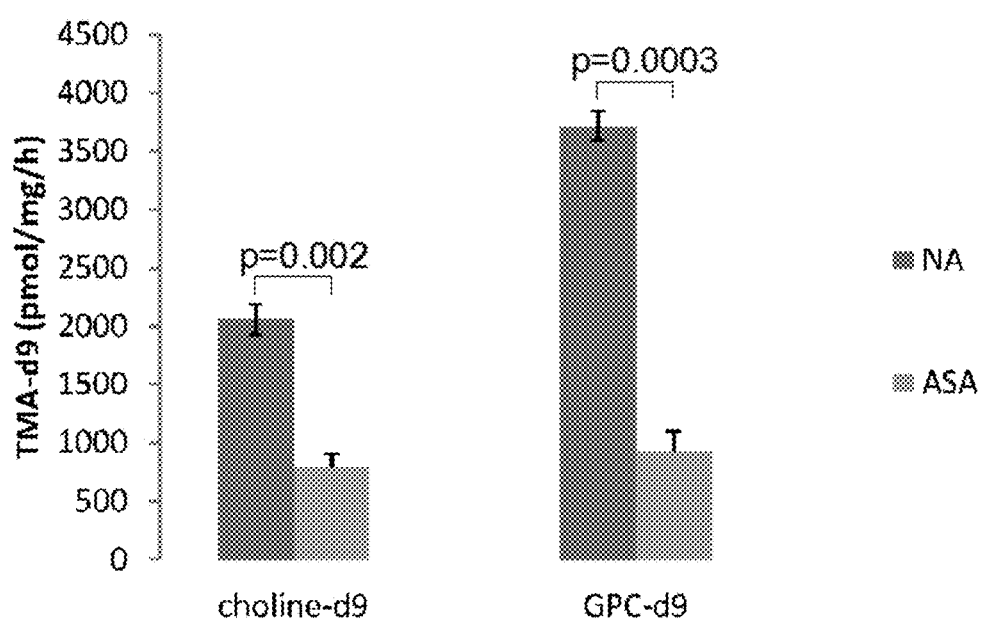
FIG. 6 shows results from Example 2 which shows that ASA inhibits choline and GPC TMA lyase activity.

Based on the findings that ASA therapy in vivo reduced TMAO, and knowledge that TMA lyases represent the major determinant of TMA and hence, TMAO levels, it was tested whether ASA directly could impact microbial TMA lyase activity. Proteus mirabilis (PM) is a microbe with abundant choline TMA lyase activity that studies suggest serves as an excellent source of microbial TMA lyase activity similar to that observed in vivo (within cecum and colon of rodents and humans, and feces of rodents and humans). Using PM lysate (PM that is lysed in a French press to break open the cell wall and release enzyme contents) as the enzyme source, the TMA lyase activity (TMA producing activity) was examined in incubations with either d9(trimethyl)choline as substrate, or d9(trimethyl) glycerophsopphocholine (GPC) as substrate. In both cases, it was noted that addition of a physiological range of ASA inhibited TMA production from the substrates. These data directly demonstrate aspirin can inhibit microbial TMA lyase activity and likely promotes TMAO reduction in vivo in part via direct inhibition in the microbial TMA lyases in vivo. The results of this work are shown in FIG. 6.

Figure 7:
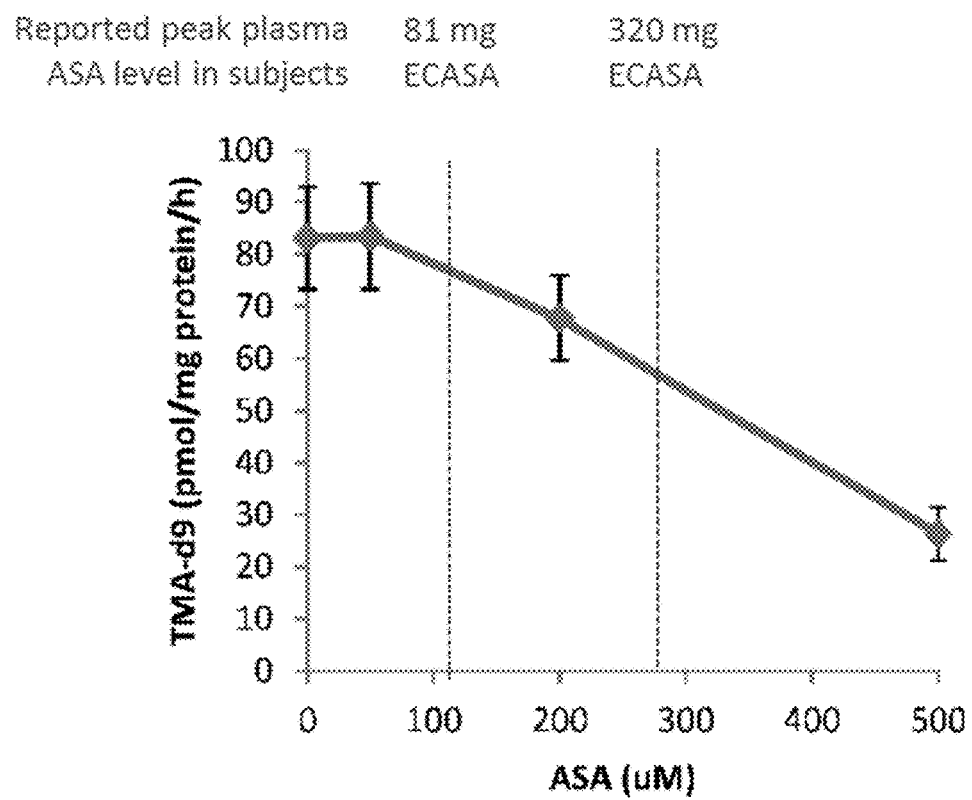
FIG. 7 shows results from Example 2 where ASA shows an inhibition in choline TMA lyase activity.

A further examination of the impact of ASA on TMA lyase activity by PM lysate was undertaken. Three mg of PM lysate was incubated with 25 uM choline and 25 uM choline(d9) in 2 ml PBS at 37 C for 20 hours. In FIG. 7, the dotted lines at 81 mg and 320 mg ASA represent reported steady state plasma levels of aspirin reported at those doses in human subjects. Thus, at a dose of one aspirin a day (320 mg) plasma levels of ASA anticipated result in approximately 40% TMA lyase inhibition. In light of this, in some embodiments, enteric coated aspirin or aspirin derivatives that have delayed absorption may be employed to treat disease since they would dissolve in the intestines past the stomach, such that the level of ASA or derivative delivered to the gut lumen will be higher. There exist even longer delayed release formulations of medications that could also be used. For example, an aspirin analog, 5 amino salicylic acid, could be used for treatment of diseases with excess TMAO production in the gut. Not only are significantly higher levels of ASA achievable within the distal gut lumen by this approach, but in addition to delayed release formulations, prodrug formulations released by gut microbe action in the ilium and colon are available and could be employed (see, e.g., Williams et al., Therap Adv Gastroenterol. July 2011; 4(4): 237-248; herein incorporated by reference, which outlines some of these formulations and applications that have been applied to 5-ASA, and thus can be applied to ASA as well).

Figure 8:
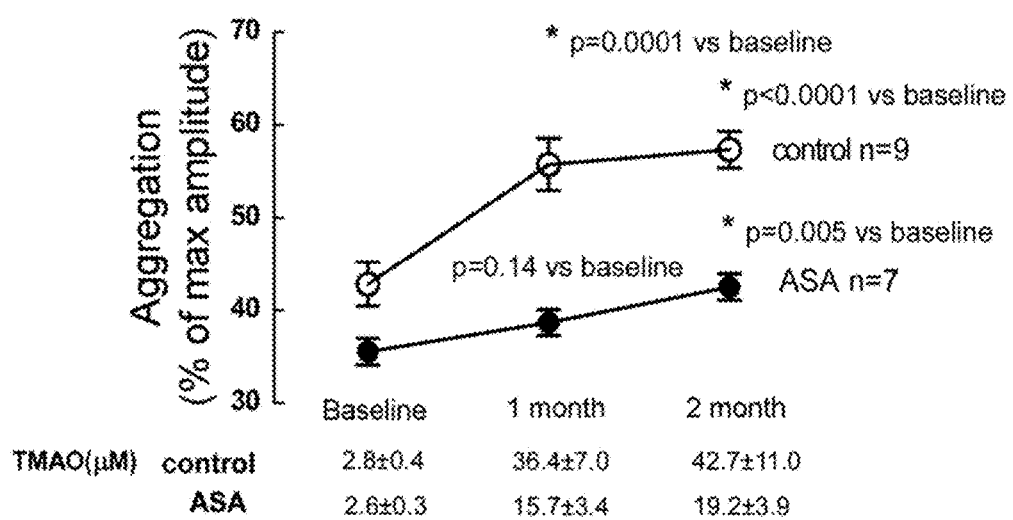
FIG. 8 shows results from Example 2, and specifically shows the effect of ASA (81 mg PO QD) on human subjects before and following chronic Choline supplementation.

In further works, human volunteer subject were enrolled in the following study. Individuals were examined at baseline for plasma TMAO and blood drawn for platelet aggregometry studies with submaximal ADP stimulation. Subjects were examined both naïve to aspirin, and then at different time after taking chronic aspirin (81 mg daily) for at least a month. As shown in FIG. 8, at baseline, looking just at those naïve to aspirin, addition of choline supplementation in the diet (equivalent to the choline content of 2 hard boiled eggs daily—see below) showed an accompanying rise in plasma TMAO levels at 1 and 2 months point, and corresponding increases in platelet aggregometrry. After washout period of at least 4 months with no choline supplement, subjects were placed on ASA daily (81 mg) and after a month of ASA, the baseline TMAO level and platelet aggregmetry measure monitored. Then, choline supplementation daily was again resumed. The impact of the choline diet on rise in TMAO was blunted. A nd the corresponding rise in platelet aggregation too was blunted. All subjects presented in FIG. 8 were omnivores.

These studies show ASA therapy helps to lower TMAO levels, and reduces prothrombotic effect associated with high choline diet (high TMAO). They underscore that TMAO elevation also may be an indication for ASA prophyllaxis therapy to prevent platelet hyperreactivity and clot risk or to treat other elevated gut TMAO diseases.

Figure 9:
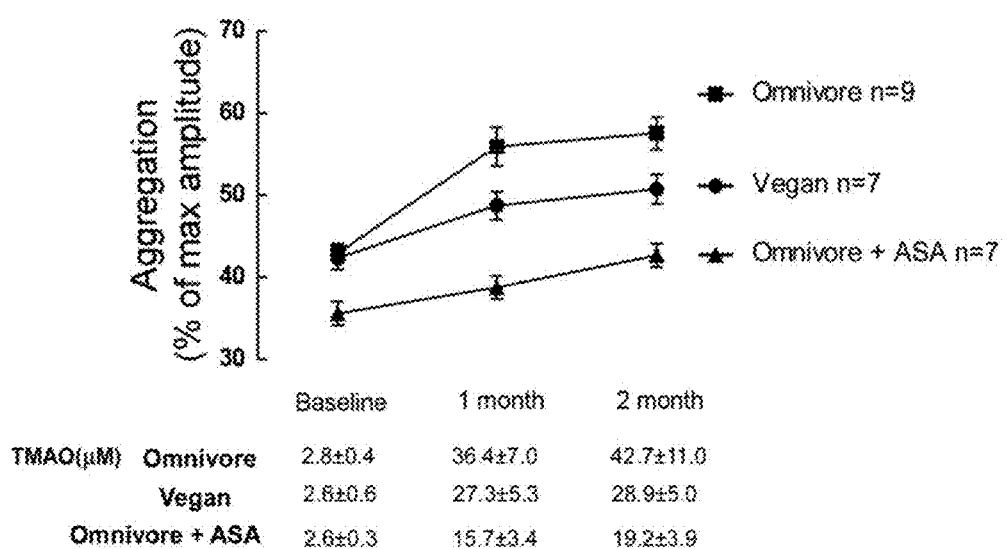
FIG. 9 shows results from Example 2, and specifically show the effect of ASA (81 mg PO QD) on human subjects before and following chronic choline supplementation.

FIG. 9 shows the same type of data as FIG. 8, except vegans were examined before vs after starting choline supplementation. Choline supplement was used in subjects (choline bitartrate, 2×500 mg/day=choline 2×205.7 mg/day), for 2 month period. Samples were collected at baseline and monthly blood were draw (1,2 months). Plasma levels of TMAO were measured and platelet aggregation in response to 5 uM ADP were measured. It was observed that the vegan diet does not protect the subject completely from elevation in TMAO from choline diet, nor a significant increase in platelet hyperresponsiveness from choline diet.

Example 3

Identification of yeaW and yeaX as TMA Lyases

Figure 12:
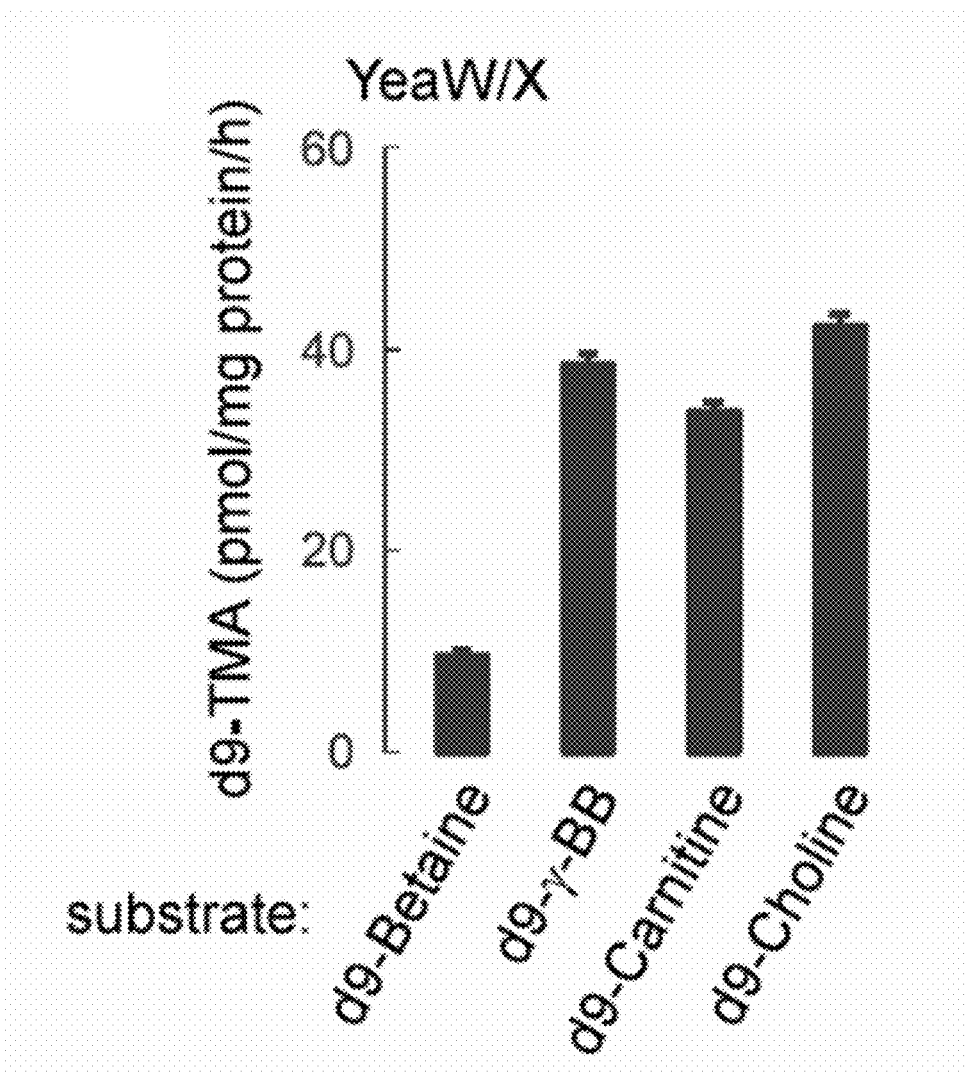
FIG. 12 shows that the recombinant microbial yeaW/X complex can catalyze the production of d9-TMA from multiple synthetic d9-trimethylamine precursors, including yBB (gamma-butyrobetaine), L-carnitine, choline, and betaine.
Figure 13:
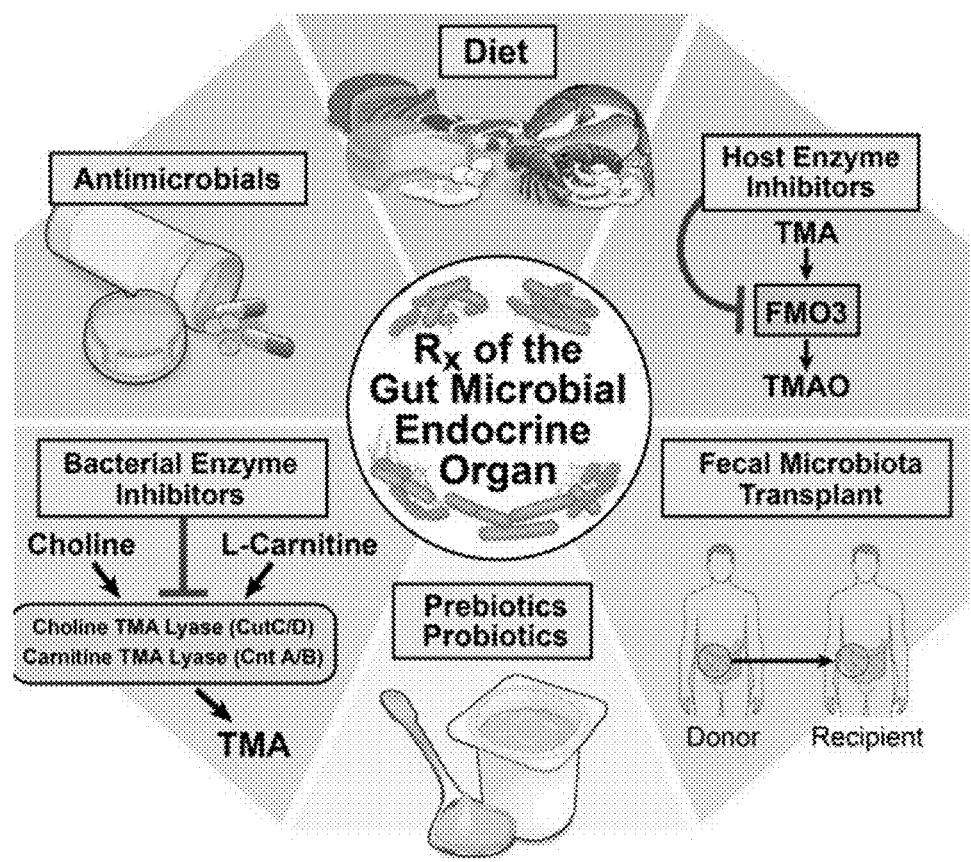
FIG. 13 provides a schematic with exemplary strategies to target the gut microbial endocrine organ (e.g., for treating kidney disease, cardiovascular disease, or other elevated TMAO related diseases). Strategies for manipulating gut microbiota include: 1) Dietary manipulation, 2) Prebiotics or Probiotics, 3) Fecal Microbiota Transplantation, 4) Antimicrobials/antibiotics, 5) Bacterial Enzyme Inhibitors (e.g., TMA lyase inhibitors), or 6) Host Enzyme Inhibitors (e.g., flavin monooxygenase 3 (FMO3) inhibitors).

As part of this example, microbial enzymes of unknown function were searched for that were clustered with those known to synthesize or use either malate or succinate (potential products formed following carntine utilization) and a presumed betaine-carnitine-choline transporter. One potential candidate was gene pair previously called yeaW/X in E. Coli DH10B (yeaW (dioxygenase), GeneID: 6060925 and yeaX (oxidoreductase), GeneID: 6060982). Using a modified pET20 plasmid, E. coli BL21pLysS was transformed with each allele and subsequently individually purified recombinant yeaW and yeaX from bacterial lysates using the 8×His metal affinity chromatography. When the purified proteins are combined, the yeaW/X complex demonstrated carnitine TMA lyase activity (monitored by d9-TMA production from d9-carnitine). Interestingly, further characterization of the recombinant microbial yeaW/X complex revealed substrate promiscuity, catalyzing production of d9-TMA from multiple synthetic d9-trimethylamine precursors (yBB, L-carnitine, choline, and betaine; FIG. 12).

The cloning, expression, isolation and characterization of yeaW/yeaX was as follows. A gene cluster consistent with the features sought was identified including the genes yeaU (dehydrogenase), GeneID: 6060908; yeaV (putative BCCT transporter), GeneID: 6060973; yeaW (dioxygenase), GeneID: 6060925 and yeaX (oxidoreductase), GeneID: 6060982. The genes for yeaW and yeaX are contiguous and were PCR'd from genomic E. Coli DH10B DNA, GeneBank: CP000948.1, nucleotides 1973260-1975405 using the following forward and reverse primers, respectively, (gene-specific sequences are underlined)

(SEQ ID NO: 5)
5' AGGAGATACC<u>ATGAGCAATCTGAGCCCTGACTTTGTACTAC</u>,
and (SEQ ID NO: 6)
5' AGGAGATATACCATG<u>TCAGACTATCAAATGTTTGAAGTACAGGTG</u>.

PCR reactions were run in 50 ul aliquots using the following temperature program: 2 min at 95° C.; 1×(20 sec at 95° C. 30 sec at 57° C., 80 sec at 68° C.); 30×(20 sec at 95° C., 30 sec at 62° C., 80 sec at 68° C.); 3 min at 68° C. and 4° C. hold. PCR reactions were fractionated on a 1% agarose gel and the PCR fragment gel-purified, quantified and used for cloning into a modified pET20 vector at the Nco I/HindIII sites using InFusion (Clontech). After DNA sequence verification of clones, pilot expression studies confirmed that the correct size protein(s) were being produced and that the lysate, but not lysate from induced native BL21 cells, had carnitine TMA-lyase activity (produced d9-TMA from d9-carnitine). The individual yeaW and yeaX genes were then PCR'd from this expression clone using gene-specific primers and cloned in-frame behind an 8X-His tag in a modified pET20 vector. Upon sequence verification, the individual epitope-tagged yeaW and yeaX alleles were transformed into E. Coli BL21 DE3 pLysS cells (Invitrogen) and individual colonies of each were expanded for growth, induction, harvesting and extract preparation, as previously described (Gogonea et al., 2010, Biochemistry 49, 7323-7343). Cells expressing 8X-His-tagged yeaW or yeaX were grown to an OD600 of 0.5, induced at room temperature with 0.4 mM IPTG for 18 h, and then harvested and protein extracts prepared using a microfluidizer, as previously described (Gogonea et al., 2010). Recombinant proteins were purified using IMAC Ni-charged resin, as previously described (Gogonea et al., 2010). Enzymatic activity was determined by incubation of the purified yeaW and eaX (30 ug each) with 100 uM deuterium labeled trimethylamine containing compounds in the presence of 200 uM NADH in 1 ml PBS at 37° C. in gas tight vials. The product, d9-TMA, was determined by LC/MS/MS as described above.

REFERENCES

1. Mafra et al., Role of altered intestinal microbiota in systemic inflammation and cardiovascular disease in chronic kidney disease. Future Microbiol 2014; 9:399-410.
2. Vaziri et al., Chronic kidney disease alters intestinal microbial flora. Kidney Int 2013; 83(2):308-15.
3. Stenvinkel and Alvestrand, Inflammation in end-stage renal disease: sources, consequences, and therapy. Semin Dial 2002; 15(5):329-37.
4. Anders et al., The intestinal microbiota, a leaky gut, and abnormal immunity in kidney disease. Kidney Int 2013; 83(6):1010-6.
5. Lee et al., Effects of AST-120 on blood concentrations of protein-bound uremic toxins and biomarkers of cardiovascular risk in chronic dialysis patients. Blood Purif 2014; 37(1):76-83.
6. Lekawanvijit et al., Cardiorenal syndrome: the emerging role of protein-bound uremic toxins. Circ Res 2012; 111(11):1470-83.
7. Ramezani and Raj. The gut microbiome, kidney disease, and targeted interventions. J Am Soc Nephrol 2014; 25(4):657-70.
8. Koeth et al., Intestinal microbiota metabolism of L-carnitine, a nutrient in red meat, promotes atherosclerosis. Nat Med 2013; 19(5):576-85.
9. Tang et al., Intestinal microbial metabolism of phosphatidylcholine and cardiovascular risk. N Engl J Med 2013; 368(17):1575-84.
10. Wang et al., Gut flora metabolism of phosphatidylcholine promotes cardiovascular disease. Nature 2011; 472 (7341):57-63.
11. Wang et al., Prognostic value of choline and betaine depends on intestinal microbiotagenerated metabolite trimethylamine-N-oxide. Eur Heart J 2014; 35(14):904-10.
12. Bennett et al. Trimethylamine-Noxide, a metabolite associated with atherosclerosis, exhibits complex genetic and dietary regulation. Cell Metab 2013; 17(1):49-60.
13. Bain et al., Accumulation of trimethylamine and trimethylamine-N-oxide in end-stage renal disease patients undergoing haemodialysis. Nephroi Dial Transplant 2006; 21(5):1300-4.
14. Bain et al., Oral L-carnitine: metabolite formation and hemodialysis. Curr Drug Metab 2006; 7(7):811-6.
15. Bell et al., Nuclear magnetic resonance studies of blood plasma and urine from subjects with chronic renal failure: identification of trimethylamine-N-oxide. Biochim Biophys Acta 1991; 1096(2):101-7.
16. Robert et al., A pair analysis of the delayed graft function in kidney recipient: the critical role of the donor. Journal of critical care 2010; 25(4):582-90.
17. Inker et al., Estimating glomerular filtration rate from serum creatinine and cystatin C. N Engl J Med 2012; 367(1):20-9.
18. Wang et al., Measurement of trimethylamine-N-oxide by stable isotope dilution liquid chromatography tandem mass spectrometry. Anal Biochem 2014; 455:35-40.
19. Pencina et al., Evaluating the added predictive ability of a new marker: from area under the ROC curve to reclassification and beyond. Stat Med 2008; 27(2):157-72; discussion 207-12.
20. Qu et al., Regulation of renal fibrosis by Smad3 thr388 phosphorylation. Am J Pathol 2014; 184(4):944-52.
21. Al-Waiz et al., The metabolism of 14C-labelled trimethylamine and its N-oxide in man. Xenobiotica 1987; 17(5): 551-8.
22. Smith et al., Metabolism and excretion of methylamines in rats. Toxicol Appl Pharmacol 1994; 125(2):296-308.
23. Zeisel et al., Conversion of dietary choline to trimethylamine and dimethylamine in rats: dose-response relationship. J Nutr 1989; 119(5):800-4.
24. Hauet et al., Proton NMR spectroscopy as a novel approach to the monitoring of citrate and trimethylamine-N-oxide excretion after kidney preservation. Transplant Proc 1997; 29(5):2323-5.
25. Le Moyec et al., Proton nuclear magnetic resonance spectroscopy of urine and plasma in renal transplantation follow-up. Nephron 1993; 65(3):433-9.
26. Serkova et al., H-NMR-based metabolic signatures of mild and severe ischemia/reperfusion injury in rat kidney transplants. Kidney Int 2005; 67(3):1142-51.
27. Foxall et al., NMR spectroscopy as a novel approach to the monitoring of renal transplant function. Kidney Int. 1993; 43(1):234-45.
28. Runyan et al., Smad3 and PKCdelta mediate TGF-beta1-induced collagen I expression in human mesangial cells. Am J Physiol Renal Physiol 2003; 285(3):F413-22.
29. Rhee et al., A combined epidemiologic and metabolomic approach improves CKD prediction. J Am Soc Nephrol 2013; 24(8):1330-8.
30. Lin et al., Associations of diet with albuminuria and kidney function decline. Clin J Am Soc Nephrol 2010; 5(5):836-43.
31. Hegazy and El-Bedewy, Effect of probiotics on pro-inflammatory cytokines and NF-kappaB activation in ulcerative colitis. World J Gastroenterol 2010; 16(33): 4145-51.

32. Seth et al., Probiotics ameliorate the hydrogen peroxideinduced epithelial barrier disruption by a PKC- and MAP kinase-dependent mechanism. Am J Physiol Gastrointest Liver Physiol 2008; 294(4):G1060-9.
33. Simenhoff et al., Biomodulation of the toxic and nutritional effects of small bowel bacterial overgrowth in end-stage kidney disease using freeze-dried *Lactobacillus acidophilus*. Miner Electrolyte Metab 1996; 22(1-3):92-6.
34. Takayama et al., *Bifidobacterium* in gastro-resistant seamless capsule reduces serum levels of indoxyl sulfate in patients on hemodialysis. Am J Kidney Dis 2003; 41(3 Suppl 1):S142-5.
35. Ranganathan et al., Probiotic amelioration of azotemia in 5/6th nephrectomized Sprague-Dawley rats. ScientificWorldJournal 2005; 5:652-60.
36. Ranganathan et al., Pilot study of probiotic dietary supplementation for promoting healthy kidney function in patients with chronic kidney disease. Adv Ther 2010; 27(9):634-47.
37. Niwa and Ise, Indoxyl sulfate, a circulating uremic toxin, stimulates the progression of glomerular sclerosis. J Lab Clin Med 1994; 124(1):96-104.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

What is claimed is:

1. A method of treating a subject with symptoms of kidney and/or cardiovascular disease comprising:
   treating a subject with a gut TMA lyase inhibitor, wherein said subject has symptoms of kidney and/or cardiovascular disease, and wherein said gut TMA lyase inhibitor comprises
   a morpholine compound with one of the following structures:

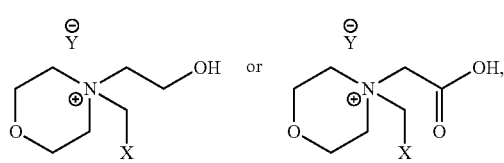

wherein, for said morpholine compound: X is H, F, Cl, Br, or I; and Y is Cl, Br, or I.

2. The method of claim 1, wherein a sample from said subject is assayed to determine levels of eGFR, eCrCl, Cystatin C, KIM1, elevated urine albumin/Creatinine ratio, trimethylamine N-oxide (TMAO), TMA, and/or a TMA-containing compound prior to and/or after said treating.

3. The method of claim 2, wherein said sample is selected from whole blood, serum, plasma, urine, and saliva.

4. The method of claim 1, wherein said morpholine compound has the following structure:

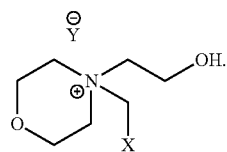

5. The method of claim 1, wherein said morpholine compound has the following structure:

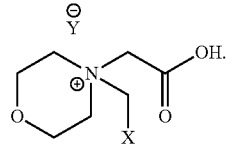

6. The method of claim 1, wherein, for said morpholine compound: X is H or F.

7. The method of claim 1, wherein, for said morpholine compound: X is Cl or Br.

8. The method of claim 1, wherein, for said morpholine compound: X is I and/or Y is Cl.

9. The method of claim 1, wherein, for said morpholine compound: Y is Br, or I.

10. The method of claim 1, wherein said morpholine compound is N-methyl-N-(2-hydroxyethyl)morpholine.

11. The method of claim 1, wherein said subject has symptoms of cardiovascular disease.

12. The method of claim 1, wherein said subject has symptoms of kidney disease.

13. The method of claim 1, wherein said morpholine compound has the following structure:

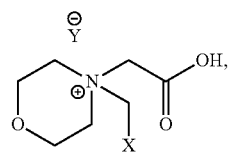

and wherein X is Cl and Y is I.

* * * * *

SEQUENCE LISTING

```
<160> NUMBER OF SEQ ID NOS: 6

<210> SEQ ID NO 1
<211> LENGTH: 1125
<212> TYPE: DNA
<213> ORGANISM: Escherichia coli

<400> SEQUENCE: 1
atgagcaatc tgagccctga ctttgtacta cccgaaaatt tttgcgctaa cccgcaagag      60
gcgtggacca ttcctgcccg tttttatacc gatcagaacg cgtttgaaca cgaaaaagag     120
aacgtcttcg ccaaaagctg gatttgcgtc gctcacagca gcgaactggc gaatgccaat     180
gattatgtga cgcgtgagat cattggcgaa agcatcgtgc tggtacgcgg tcgtgataag     240
gttttgcgcg cgttctataa cgtgtgtccg caccgtggtc atcagttgtt gagcggtgaa     300
ggaaaagcaa aaatgtgat taccctgcccg tatcacgcat gggcattcaa actcgatggc     360
aacctggccc atgcacgtaa ctgcgaaaac gtcgccaatt tcgatagcga caaagcgcaa     420
ctggttccgg tgcgtctgga agaatatgcc ggattcgtct tcatcaacat ggaccccaac     480
gccaccagcg tagaagatca attacccggc ctgggcgcga aagtgctgga agcctgcccg     540
gaagtccacg atctgaaact ggcggcccgc tttaccaccc gcacgcctgc caactggaag     600
aacattgtcg ataactatct cgagtgctat cactgtggtc cggcgcatcc aggtttctcc     660
gactccgtac aggttgatcg ttactggcac accatgcacg gtaactggac gctgcaatac     720
ggtttcgcca aaccgtccga acagtcgttt aaatttgaag agggtacgga tgcggcattc     780
cacggtttct ggctgtggcc gtgcacgatg ctgaacgtca ccccgatcaa agggatgatg     840
acggtcattt atgaattccc ggtggattct gaaactaccc tgcaaaacta cgatatttac     900
ttcaccaatg aagagttaac cgacgagcaa aaatcgctga ttgagtggta tcgcgatgtg     960
ttccgtccgg aagatttacg tctggttgaa agcgtacaga aagggctgaa atcgcgtggc    1020
tatcgtggtc aggggcgcat catggccgac agtagcggta gtggcatttc cgaacatggt    1080
atcgcccatt tccataatct gctggcgcag gtgtttaagg actaa                     1125

<210> SEQ ID NO 2
<211> LENGTH: 374
<212> TYPE: PRT
<213> ORGANISM: Escherichia coli

<400> SEQUENCE: 2
```

Met Ser Asn Leu Ser Pro Asp Phe Val Leu Pro Glu Asn Phe Cys Ala
1               5                   10                  15

Asn Pro Gln Glu Ala Trp Thr Ile Pro Ala Arg Phe Tyr Thr Asp Gln
            20                  25                  30

Asn Ala Phe Glu His Glu Lys Glu Asn Val Phe Ala Lys Ser Trp Ile
                35                  40                  45

Cys Val Ala His Ser Ser Glu Leu Ala Asn Ala Asn Asp Tyr Val Thr
    50                  55                  60

Arg Glu Ile Ile Gly Glu Ser Ile Val Leu Val Arg Gly Arg Asp Lys
65                  70                  75                  80

Val Leu Arg Ala Phe Tyr Asn Val Cys Pro His Arg Gly His Gln Leu
                85                  90                  95

Leu Ser Gly Glu Gly Lys Ala Lys Asn Val Ile Thr Cys Pro Tyr His
                100                 105                 110

Ala Trp Ala Phe Lys Leu Asp Gly Asn Leu Ala His Ala Arg Asn Cys
            115                 120                 125

Glu Asn Val Ala Asn Phe Asp Ser Asp Lys Ala Gln Leu Val Pro Val
    130                 135                 140

Arg Leu Glu Glu Tyr Ala Gly Phe Val Phe Ile Asn Met Asp Pro Asn
145                 150                 155                 160

Ala Thr Ser Val Glu Asp Gln Leu Pro Gly Leu Gly Ala Lys Val Leu
                165                 170                 175

Glu Ala Cys Pro Glu Val His Asp Leu Lys Leu Ala Ala Arg Phe Thr
            180                 185                 190

Thr Arg Thr Pro Ala Asn Trp Lys Asn Ile Val Asp Asn Tyr Leu Glu
                195                 200                 205

Cys Tyr His Cys Gly Pro Ala His Pro Gly Phe Ser Asp Ser Val Gln
    210                 215                 220

Val Asp Arg Tyr Trp His Thr Met His Gly Asn Trp Thr Leu Gln Tyr
225                 230                 235                 240

Gly Phe Ala Lys Pro Ser Glu Gln Ser Phe Lys Phe Glu Glu Gly Thr
                245                 250                 255

Asp Ala Ala Phe His Gly Phe Trp Leu Trp Pro Cys Thr Met Leu Asn
            260                 265                 270

Val Thr Pro Ile Lys Gly Met Met Thr Val Ile Tyr Glu Phe Pro Val
    275                 280                 285

Asp Ser Glu Thr Thr Leu Gln Asn Tyr Asp Ile Tyr Phe Thr Asn Glu
    290                 295                 300

Glu Leu Thr Asp Glu Gln Lys Ser Leu Ile Glu Trp Tyr Arg Asp Val
305                 310                 315                 320

Phe Arg Pro Glu Asp Leu Arg Leu Val Glu Ser Val Gln Lys Gly Leu
                325                 330                 335

Lys Ser Arg Gly Tyr Arg Gly Gln Gly Arg Ile Met Ala Asp Ser Ser
                340                 345                 350

Gly Ser Gly Ile Ser Glu His Gly Ile Ala His Phe His Asn Leu Leu
                355                 360                 365

Ala Gln Val Phe Lys Asp
        370

<210> SEQ ID NO 3
<211> LENGTH: 966
<212> TYPE: DNA
<213> ORGANISM: Escherichia coli

<400> SEQUENCE: 3

```
atgtcagact atcaaatgtt tgaagtacag gtgagccagg ttgaacccct taccgaacag    60
gtgaaacgct tcacgctggt ggcaaccgat ggcaaaccat acctgcgtt taccggagga   120
agtcacgtca ttgtgcagat gagcgatggt gataaccagt acagcaatgc gtattcacta   180
ctgagttcgc cgcatgacac ctcttgttat cagattgccg ttcggctgga ggaaaactcg   240
cgcggcggtt cccgcttttt gcatcagcag gtaaaagtgg gcgatcggtt aacgatttca   300
acgcctaata acctgtttgc gctaattccc tcagccagaa agcatctgtt tatcgcgggc   360
ggtattggta tcaccccttt cctgtcgcac atggcagagc tgcaacacag cgacgtcgac   420
tggcagctac attactgctc gcgaaatcca gaaagttgcg catttcgtga tgagctagtc   480
cagcatccgc aggctgagaa agtccatttg catcattcat caaccggaac acgactggaa   540
ttagcgcgat tattggcgga tatcgaacct ggcacacacg tttatacctg tggccccgag   600
gcgctaattg aagcggtaag aagtgaagct gcgcgtctgg acatcgccgc cgatacgctg   660
cactttgagc aatttgctat cgaagacaaa accggcgatg catttaccct ggtgcttgcc   720
cgttccggaa aagagtttgt ggtgccggaa gagatgacta ttttgcaggt tattgaaaat   780
aataaagccg cgaaagtgga atgtttatgt cgtgaagggg tatgcggaac ctgcgaaaca   840
gcaatactgg aaggtgaagc tgaccatcgg gatcaatatt ttagcgatga gagcgtgcc    900
agccagcaaa gtatgttgat ctgttgttcg cgtgcgaagg gtaaacgcct ggtgttggat   960
ttgtag                                                              966
```

<210> SEQ ID NO 4
<211> LENGTH: 321
<212> TYPE: PRT
<213> ORGANISM: Escherichia coli

<400> SEQUENCE: 4

```
Met Ser Asp Tyr Gln Met Phe Glu Val Gln Val Ser Gln Val Glu Pro
1               5                   10                  15

Leu Thr Glu Gln Val Lys Arg Phe Thr Leu Val Ala Thr Asp Gly Lys
            20                  25                  30

Pro Leu Pro Ala Phe Thr Gly Gly Ser His Val Ile Val Gln Met Ser
        35                  40                  45

Asp Gly Asp Asn Gln Tyr Ser Asn Ala Tyr Ser Leu Leu Ser Ser Pro
    50                  55                  60

His Asp Thr Ser Cys Tyr Gln Ile Ala Val Arg Leu Glu Glu Asn Ser
65                  70                  75                  80

Arg Gly Gly Ser Arg Phe Leu His Gln Gln Val Lys Val Gly Asp Arg
                85                  90                  95

Leu Thr Ile Ser Thr Pro Asn Asn Leu Phe Ala Leu Ile Pro Ser Ala
            100                 105                 110

Arg Lys His Leu Phe Ile Ala Gly Gly Ile Gly Ile Thr Pro Phe Leu
        115                 120                 125

Ser His Met Ala Glu Leu Gln His Ser Asp Val Asp Trp Gln Leu His
    130                 135                 140

Tyr Cys Ser Arg Asn Pro Glu Ser Cys Ala Phe Arg Asp Glu Leu Val
145                 150                 155                 160

Gln His Pro Gln Ala Glu Lys Val His Leu His His Ser Ser Thr Gly
                165                 170                 175

Thr Arg Leu Glu Leu Ala Arg Leu Leu Ala Asp Ile Glu Pro Gly Thr
            180                 185                 190
```

```
His Val Tyr Thr Cys Gly Pro Glu Ala Leu Ile Glu Ala Val Arg Ser
            195                 200                 205

Glu Ala Ala Arg Leu Asp Ile Ala Ala Asp Thr Leu His Phe Glu Gln
    210                 215                 220

Phe Ala Ile Glu Asp Lys Thr Gly Asp Ala Phe Thr Leu Val Leu Ala
225                 230                 235                 240

Arg Ser Gly Lys Glu Phe Val Val Pro Glu Glu Met Thr Ile Leu Gln
                245                 250                 255

Val Ile Glu Asn Asn Lys Ala Ala Lys Val Glu Cys Leu Cys Arg Glu
                260                 265                 270

Gly Val Cys Gly Thr Cys Glu Thr Ala Ile Leu Glu Gly Glu Ala Asp
            275                 280                 285

His Arg Asp Gln Tyr Phe Ser Asp Glu Glu Arg Ala Ser Gln Gln Ser
            290                 295                 300

Met Leu Ile Cys Cys Ser Arg Ala Lys Gly Lys Arg Leu Val Leu Asp
305                 310                 315                 320

Leu

<210> SEQ ID NO 5
<211> LENGTH: 41
<212> TYPE: DNA
<213> ORGANISM: Artificial sequence
<220> FEATURE:
<223> OTHER INFORMATION: Foward DNA primer

<400> SEQUENCE: 5
aggagatacc atgagcaatc tgagccctga ctttgtacta c                    41

<210> SEQ ID NO 6
<211> LENGTH: 45
<212> TYPE: DNA
<213> ORGANISM: Artificial sequence
<220> FEATURE:
<223> OTHER INFORMATION: Reverse DNA Primer

<400> SEQUENCE: 6
aggagatata ccatgtcaga ctatcaaatg tttgaagtac aggtg                45
```